(12) United States Patent
Boehm et al.

(10) Patent No.: US 7,091,028 B1
(45) Date of Patent: Aug. 15, 2006

(54) METHOD FOR DIRECTED PACKAGING OF MOLECULAR SUBSTANCES IN PROTEIN SHELLS

(75) Inventors: Gerald Boehm, Halle (DE); Dirk Esser, Cambridge (GB); Ulrich Schmidt, West Leederville (AU)

(73) Assignee: ACGT ProGenomics AG, Halle Saale (DE)

( * ) Notice: Subject to any disclaimer, the term of this patent is extended or adjusted under 35 U.S.C. 154(b) by 462 days.

(21) Appl. No.: 10/129,207

(22) PCT Filed: Nov. 3, 2000

(86) PCT No.: PCT/EP00/10878

§ 371 (c)(1),
(2), (4) Date: Oct. 21, 2002

(87) PCT Pub. No.: WO01/32852

PCT Pub. Date: May 10, 2001

(30) Foreign Application Priority Data

Nov. 3, 1999 (DE) ................................ 199 52 982

(51) Int. Cl.
*C12N 7/02* (2006.01)
(52) U.S. Cl. .................... 435/235.1; 424/450
(58) Field of Classification Search ............... None
See application file for complete search history.

(56) References Cited

FOREIGN PATENT DOCUMENTS

| DE | 36 36 540 A1 | 4/1988 |
|----|--------------|--------|
| WO | WO 99/25324 A1 | 5/1999 |

OTHER PUBLICATIONS

Ou, W. et al."The Major Capsid Protein, VP1, of Human JC Virus Expressed in *Escherichia coli* is Able to Self-assemble into a Capsid-like Particle and Deliver Exogenous DNA into Human Kidney Cells," *J. of General Virology* 1999, pp. 39-46, vol. 80.

Schneider, J. et al. "Inhibition of HIV-1 in Cell Culture by Synthetic Humate Analogues Derived from Hydroquinone: Mechanism of Inhibition," *Virology* 1996, pp. 389-395, vol. 218.

*Primary Examiner*—James Ketter
(74) *Attorney, Agent, or Firm*—Townsend and Townsend and Crew LLP

(57) ABSTRACT

The invention relates to a method for packaging molecular substances in protein shells, comprising the following steps: binding a protein shell fragment, via a first region to a matrix; bringing the protein shell fragment bound to the matrix into contact with the molecular substance, in order to bind the molecular substance to a second region of the protein shell fragment; separating the protein shell fragment with the bonded molecular substance, or the part thereof which contains the bonded molecular substance, from the matrix and assembling the separated protein shell fragments, or the part thereof which contains the bonded molecular substance, with other protein shell fragments to form a protein shell, whereby the separation and assembly can be carried out in any order.

23 Claims, 7 Drawing Sheets

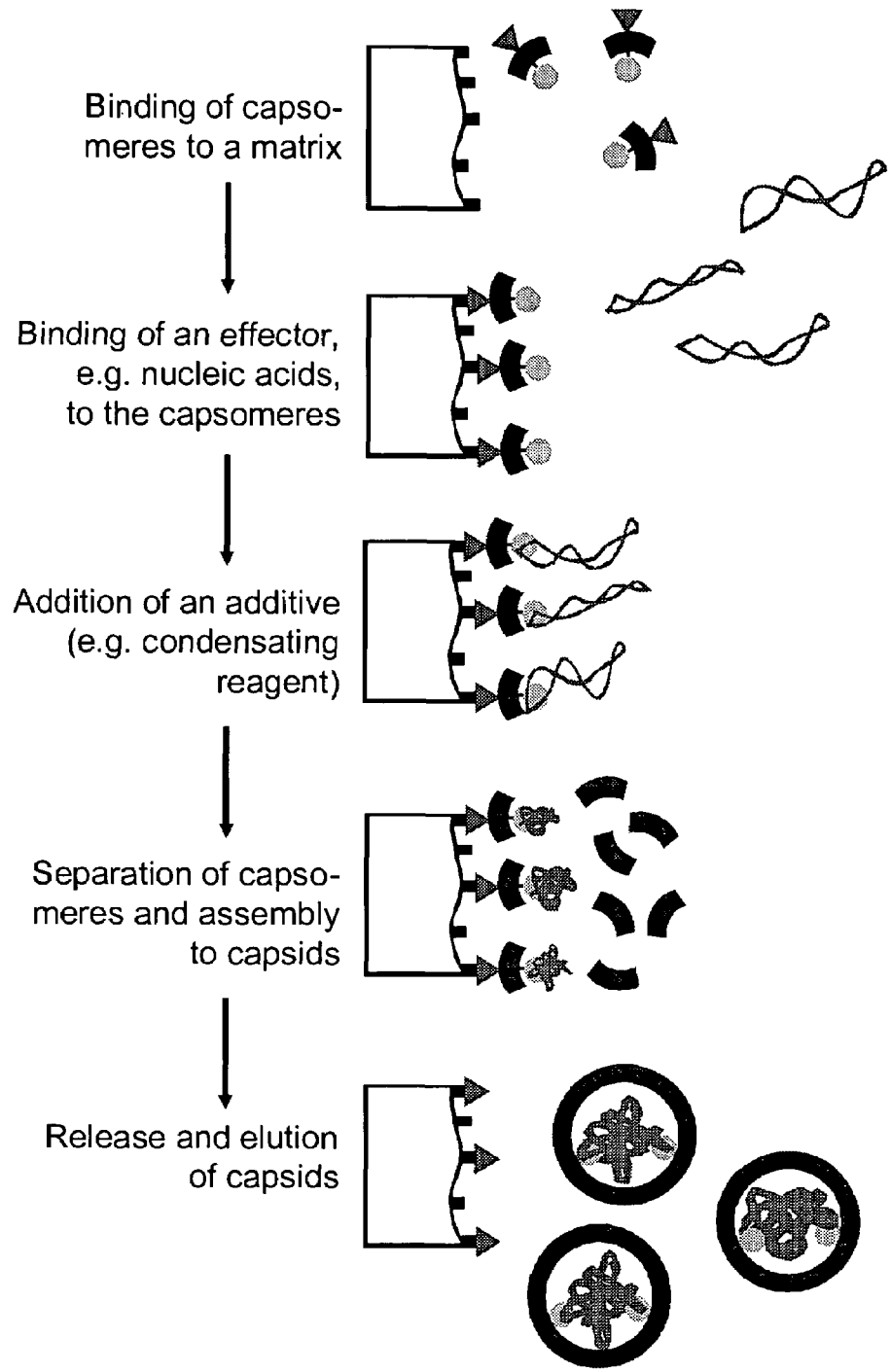
Figure 1. Scheme for the directed packaging of molecular substances on a matrix.

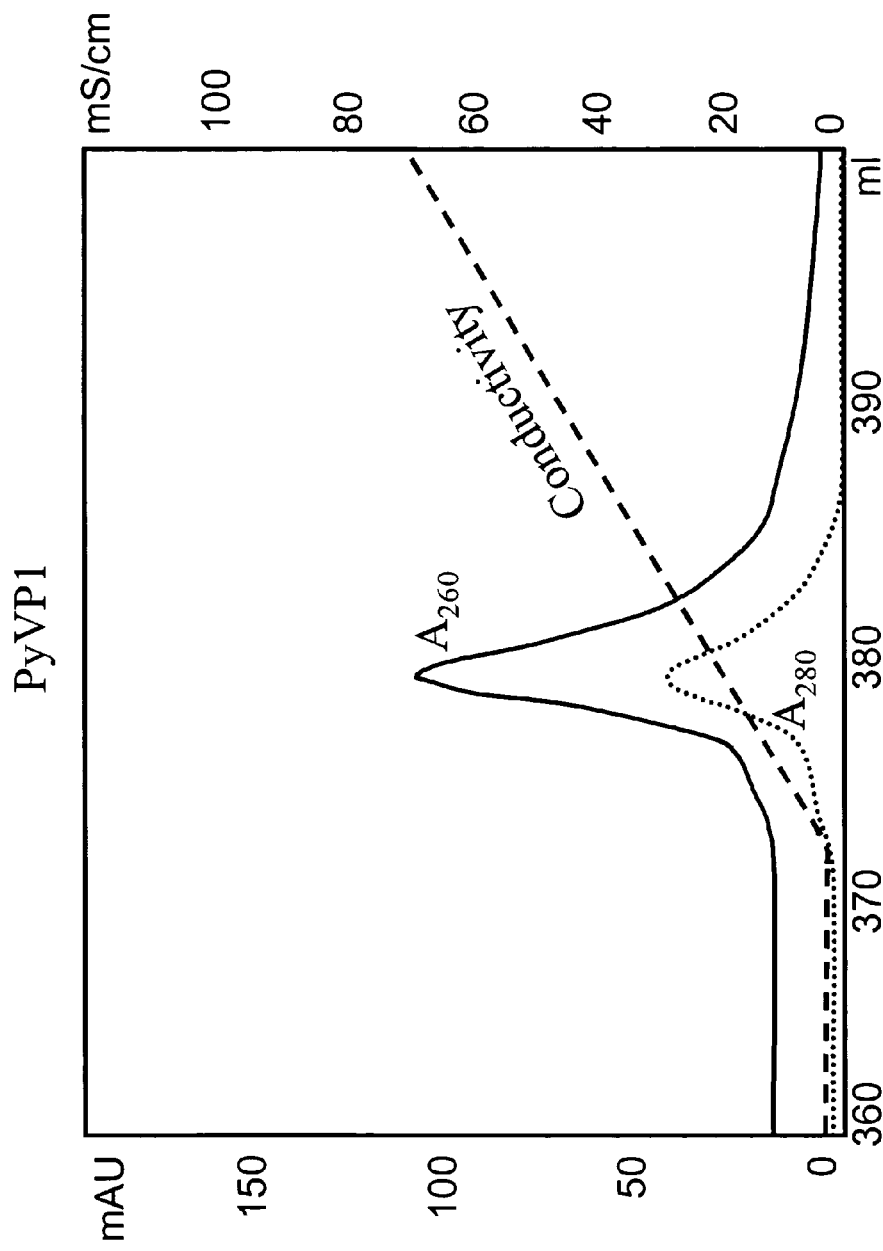
Figure 2a. Elution profile of immobilized nucleic acids on polyomavirus VP1.

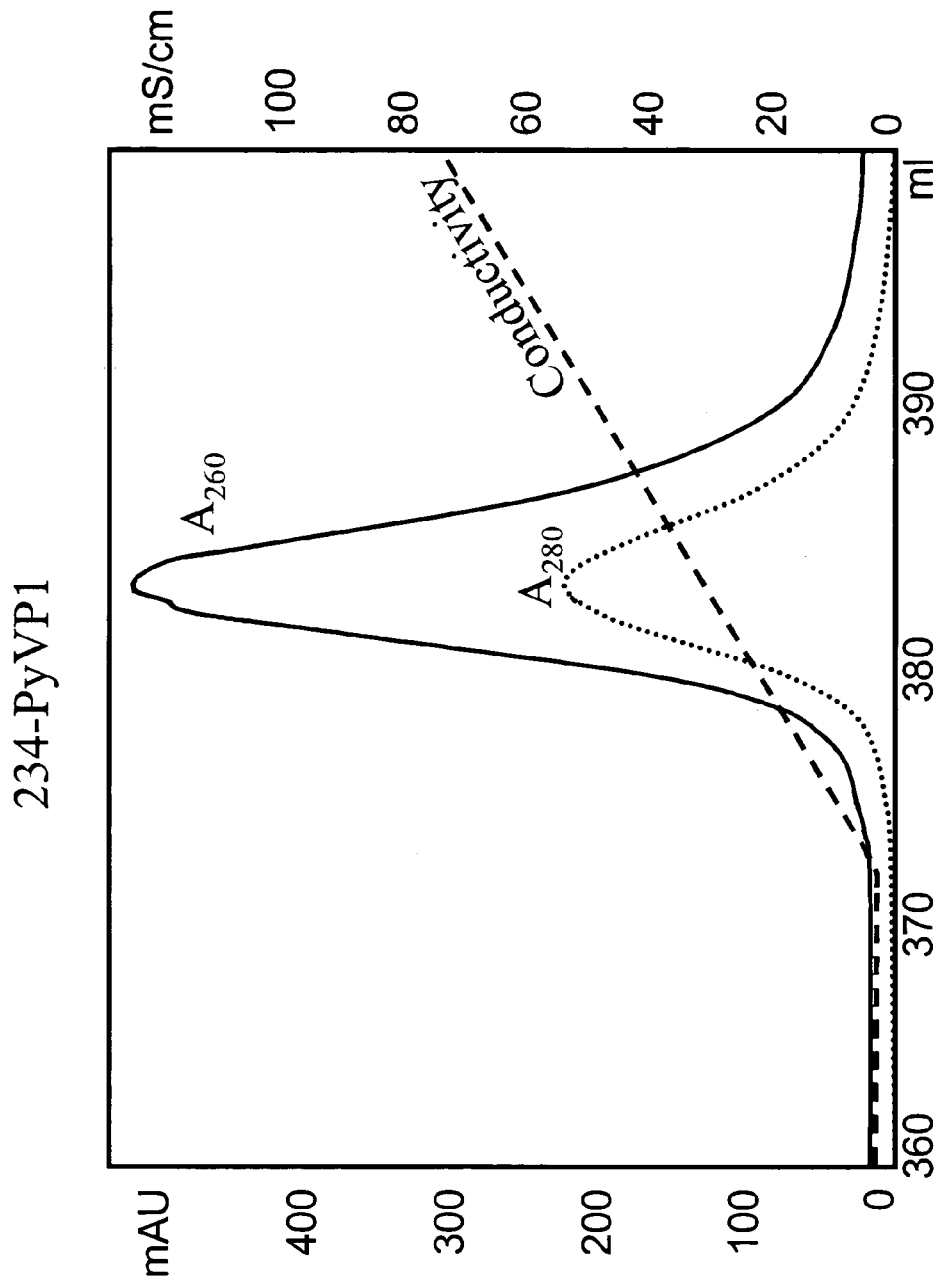
Figure 2b. Elution profile of immobilized nucleic acids on 234-PyVP1.

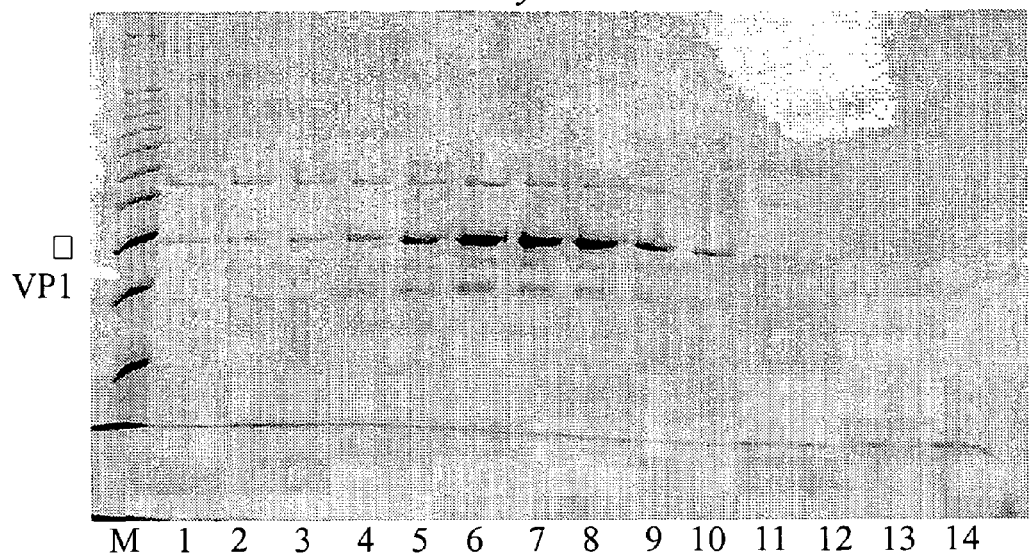
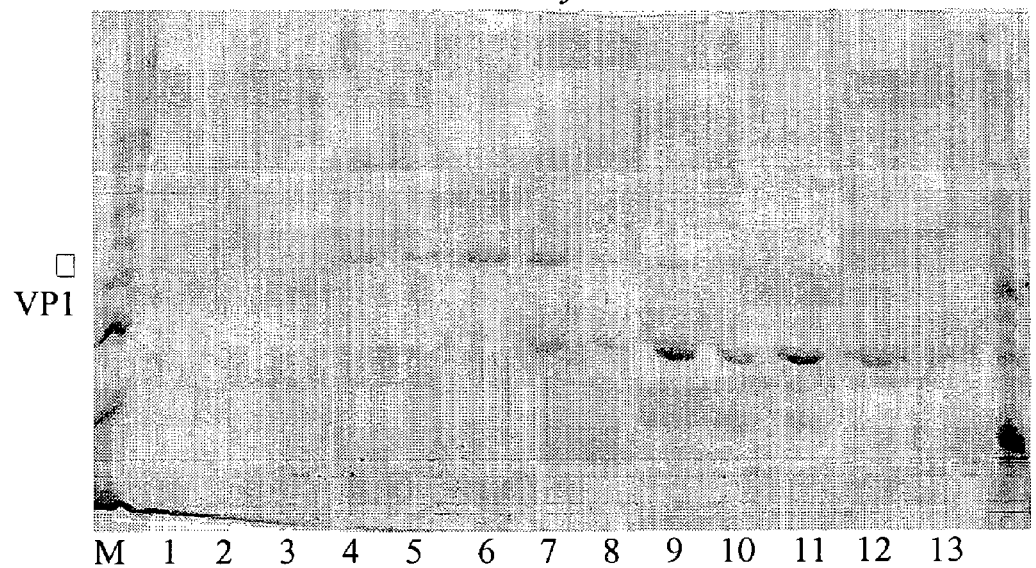
Figure 3. Gel elektrophoretic analysis of the capsomer fractions.

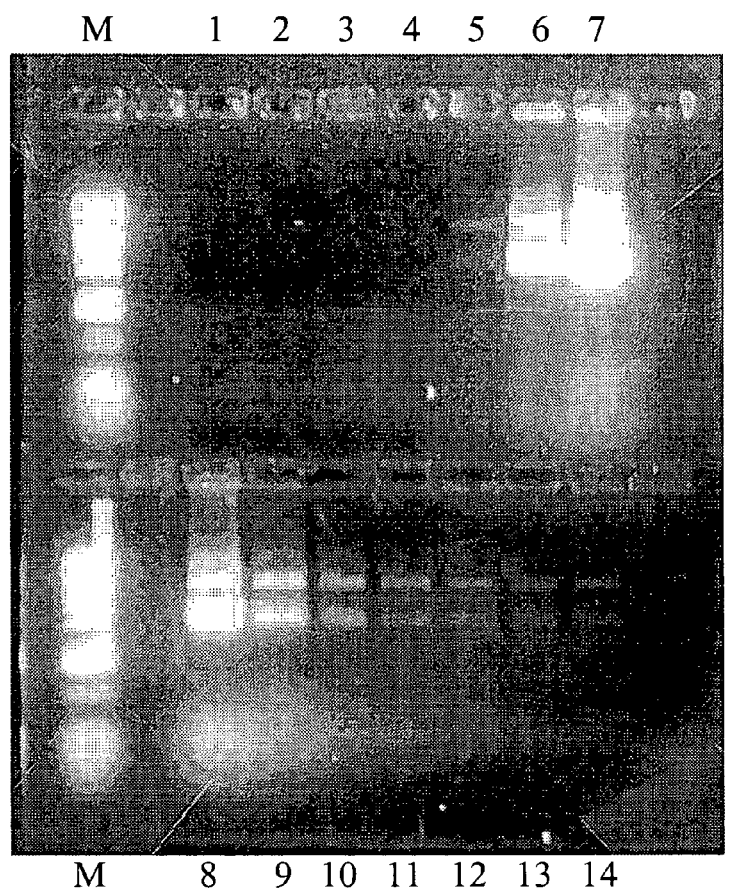
Figure 4a. Analysis of the nucleic acid loading of polyomavirus VP1.

Figure 4b. Analysis of the nucleic acid loading of 234-PyVP1.

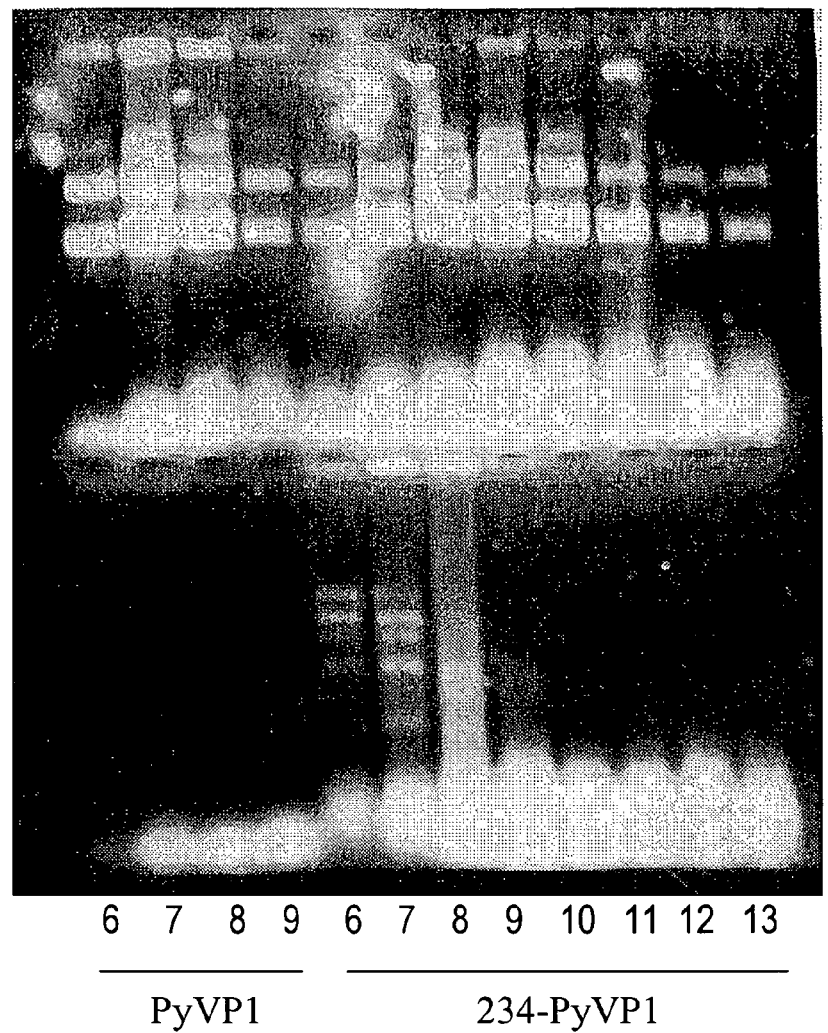
Figure 5. Analysis of packaging efficiency.

METHOD FOR DIRECTED PACKAGING OF MOLECULAR SUBSTANCES IN PROTEIN SHELLS

This application is the national phase under 35 U.S.C. §371 of PCT/EP00/10878, filed Nov. 3, 2000, which claims priority to German patent application No. 19952982.5, filed Nov. 3, 1999.

The present invention relates to a procedure for packaging of molecular substances in protein shells.

AREA OF THE INVENTION AND STATE OF THE TECHNOLOGY

The in vitro packaging of nucleic acids or other drugs in protein shells has a high impact for biotechnological usage, especially for the insertion of heterologous DNA in eukaryotic cells for studies of the cell biology, or for medical usage for therapeutic purposes within a gene therapy. Thereby often simple, recombinantly produced viral envelopes are used for in vitro-packaging, since they represent natural nucleic acid packaging units; corresponding systems are termed as virus-like gene transfer systems. They are counted to the physical gene transfer systems, in contrast to the liposomal systems (based on different formulations of mostly cationic lipids and detergents which are assembled to liposomes and related structures) and the viral vector systems. The viral vector systems for gene transfer and gene therapy are today mostly derived from retroviruses, but increasingly other types of viruses (herpes virus, adenovirus, adeno-associated virus) are used, too. A summary of the different gene transfer systemes can be found in the first TAB report "Stand und Perspektiven naturwissenschaftlicher und medizinischer Problemlösungen bei der Entwicklung gentherapeutischer Heilmethoden" of the "Büro für Technikfolgenabschätzung" at the German Parliament (TAB report No. 25, 1994).

The natural packaging of nucleic acids in viral envelopes is a complex process, in which many factors, among others also some from the host cell, interact with each other. The process is in most of the cases still poorly understood. That is why most of the in vitro-packaging systems based on it work only with comparatively low efficiency and yield. Apart from this, a size limit concerning the DNA which has to be packed is usually observed for the in vitro procedure. The low efficiency of the in vitro method in comparison to the natural packaging process at virus formation is often caused by the absence of specific host factors in the artificial in vitro system.

A special obstruction is also the length of the uncondensed DNA of usual size in aqueous solution. Under these conditions, plasmids reach (due to the repulsion of negative charge of the comparatively stiff polyphosphate backbone), at a coding length of 5 kbp, a linear (hydrodynamic) length in the range of micrometers. With typical icosaedric viral envelope diameters of 30 to 100 nm it is clear that an efficient packaging is hardly possible without DNA condensation. On the other hand, the simple addition of condensation agents to the capsid or capsomer solution does not cogently lead to improved packaging efficiency. DNA condensed in such a way tends in typical concentration ranges to the formation of so called toroids, which are ring-shaped, high-molecular aggregates, that have a diameter of several micrometers and therefore, due to their size, cannot be packed in common virus-like protein shells.

Finally, there are only few described procedures for packaging of nucleic acid in virus-like particles in vitro, that means without the usage of special packaging cell lines. A well-characterized system with respect to this is the murine Polyomavirus (cf. S. N. Slilaty & H. V. Aposhian, "Gene transfer by Polyoma-like particles assembled in a cell-free system", *Science* 220, S. 725–727, 1983; J. Forstova, N. Krauzewicz, V. Sandig, J. Elliott, Z. Palkova, M. Strauss & B. E. Griffin, "Polyoma virus pseudocapsids as efficient carriers of heterologous DNA into mammalian cells", *Hum. Gene Ther.* 6, S. 297–306, 1995). The pentameric coat protein VP1 of the Polyomavirus (PyVP1) can form under suitable solvent conditions (increase of the ionic strength, addition of calcium or ammonium sulphate, choice of a suitable pH value) in vitro virus-like structures, which are in structure mostly identical to the virus capsids originating under biological conditions. A loading of a capsid produced in this way can be initiated by a procedure known for a long time as the osmotic shock method (S. M. Barr, K. Keck & H. V. Aposhian, "Cell-free assembly of a Polyoma-like particle from empty capsid and DNA", *Virology* 96, S. 656–659, 1979; S. N. Slilaty, K. I. Berns & H. V. Aposhian, "Polyoma-like particle: characterization of the DNA encapsidated in vitro by Polyoma empty capsids", *J. Biol. Chem.* 257, S. 6571–6575, 1982). Here, nucleic acid molecules incubated with capsids are protected against nuclease digestion. Probably this happens less for a packaging into the interior of the capsid, but rather as an apposition of the nucleic acid onto the surface of the capsid. Moreover, this method of the osmotic shock is very inefficient. Recent analyses show that in contrast to former assumptions with respect to the method of the osmotic shock, indeed single nucleic acids in solution can be encapsidated statistically into the capsid (H. Braun, K. Boller, J. Lower, W. M. Bertling & A. Zimmer, "Oligonucleotide and plasmid DNA packaging into Polyoma VP1 virus-like particles expressed in *Escherichia coli*", *Biotechnol. Appl. Biochem.* 29, S. 31–43, 1999); the efficiency and specificity of the encapsidation is low here, too, due to the lack of a directed but instead a rather statistic nature of the method in solution.

Therefore, the task of the present invention is to remove the named disadvantages of the present state of the technology.

This is solved according to the invention by a procedure according to claim 1 for inclusion of molecular substances in protein shells with the following steps:

binding of a protein shell fragment by a first region to a matrix;

bringing the matrix-bound protein shell fragment in contact with the molecular substance, in order to bind the molecular substance to a second region of the protein shell fragment;

separation of the protein shell fragment with the bound molecular substance, or of one region of the protein shell fragment which contains the bound molecular substance, from the matrix; and assembly of the separated protein shell fragment or a part of it which contains the bound molecular substance, with other protein shell fragments to a protein shell, whereby the separation and the assembly can be performed in any order.

Advantageous configurations of the method result from the subclaims and from the description.

DESCRIPTION

The present invention relates to the production of transport systems, among other also suitable for gene transfer, transfer of drugs, and gene therapy, which are derived from in vitro produced protein shells. In methods according to the current state of the technology a type of coat protein or several coat protein species of—mostly icosaedric—viruses or phages are forced by suitable choice of the solvent conditions to assemble to regular structures which enclose in their interior a protected cavity. The cavity formed by the protein shell can be used for the transport of molecular substances. In the case of a conventional gene transfer applications a suitable DNA plasmid which codes for one or more genes is used as the substance which has to be transported in cells. The in vitro packaging of nucleic acids in virus-like particles, for instance in Polyomavirus particles in solution, has been analyzed for a long time (cf. S. N. Slilaty, K. I. Berns, & H. V. Aposhian, "Polyoma-like particle: characterization of the DNA encapsidated in vitro by Polyoma empty capsids", *J. Biol. Chem.* 257, S. 6571–6575, 1982). Apart from viruses, phages can also be used in principle for this artificial packaging.

The directed insertion of drugs, especially of DNA-based expression plasmids, in virus-like particles is actually ineffective according to the current state of the technology. In case of the Polyomavirus coat protein VP1, for example, the current procedure for the loading of virus-like particles with DNA is the usage of the osmotic shock procedure which is inefficient and by which possibly only an external loading of the DNA onto the artificial virus-like capsids occurs. The present invention relates to a new procedure for directed packaging of molecular substances, for instance of nucleic acid, peptides, proteins or other active substances, into the protected interior of protein shells.

The method which is described in the present invention, can in principle be used for directed and highly efficient packaging of molecular substances of many different kinds into shells, for example derived from viruses or phages. The encapsidation of such molecular substances can be used for many technical or medical and therapeutical processes.

In the method according to the invention, a region of the protein shell (in this invention termed as protein shell fragment) is bound, respectively immobilized, by a first part (region) to a matrix. A second region of the protein shell fragment, to which the molecular substance can bind, is at the same time unfixed and is freely accessible for the molecular substance which has to be packaged. The protein shell fragment bound, respectively immobilized, to the matrix is now brought into contact with the molecular substance which has to be packaged. Then the separation of the loaded protein shell fragment from the matrix is induced. Before this, simultaneously, or afterwards, the assembly or complexation of the loaded protein shell fragment with other protein shell fragments occurs. The molecular substance can be packaged with this procedure into the coat in a directed way. Also, with the method according to the invention molecular substances can be packaged which tend to aggregation in solution or show other unfavourable features. FIG. 1 shows schematically and as an example a possible model of the invention in which virus capsomers are used as protein shell fragments.

For molecular substances which have to be packed according to the invention single-stranded or double-stranded DNA, single-stranded or double-stranded RNA, peptides, peptide hormones, proteins, protein domains, glycoproteins, ribozymes, PNA (Peptide Nucleic Acid), pharmaceutical active compounds, for example with hydrophilic or hydrophobic or amphiphilic character, nucleotides, hormones, lipids, or carbohydrates can be used. Of advantage is DNA in the form of linear or circular plasmids, single-stranded or double-stranded oligonucleotides, chromosomes or chromosome fragments, or proteins in the form of antibodies, single-chain antibodies, enzymes or marker proteins, or RNA in form of antisense-RNA, ribozymes, catalytic RNA, or coding mRNA.

If needed, further additions, as for example free subunits of the coat protein, variants of it, or nucleic acid-condensation agents, can be used in the progress of the method.

In case of the packaging of DNA as a molecular substance, which is in uncondensed form too large for a packaging in protein shells, can, according to the invention, one or more condensation substances be added after the contact of the the matrix-bound protein shell fragment with the molecular substance, in order to get a more compact structure of the molecular substance.

The procedure described in the present invention for packaging of molecular substances is not limited to icosahedral viruses and phages as protein shells, but can also be applied on morphologically different shaped viruses and phages as well as on macromolecular associations with an inner cavity like proteasomes or chaperones. The following table 1 shows the viruses and phages with their respective morphology summed up which can be used according to the invention. Especially well analysed is in this case the group of icosahedral viruses.

TABLE 1

Viruses and phages usable as protein shells according to the invention.

| morphology | virus or phage |
| --- | --- |
| amorphous respectively unknown structure | Umbravirus; Tenuivirus |
| bacilliform | Baculoviridae; Badnavirus; Barnaviridae; Filoviridae; Rhabdoviridae |
| filamentous | Capillovirus; Carlavirus; Closterovirus; Furovirus; Inoviridae; Lipothrixviridae; Potexvirus; Potyviridae; Tobamovirus; Tobravirus; Polydnaviridae |
| helical | Hordeivirus; Paramyxoviridae; Trichovirus |
| icosahedral | Adenoviridae; Astroviridae; Birnaviridae; Bromoviridae; Caliciviridae; Caulimovirus; Circoviridae; Comoviridae; Corticoviridae; Dianthovirus; Enamovirus; Hepadnaviridae; Herpesviridae; Idaeovirus; Iridoviridae; Lviviridae; Luteovirus; Machlomovirus; Marafivirus; Microviridae; Necrovirus; Nodaviridae; Papovaviridae; Partitiviridae; Parvoviridae; Phycodnaviridae; Picornaviridae; Reoviridae; Rhizidiovirus; Sequiviridae; Sobemovirus; Tectiviridae; Tetraviridae; Tombusviridae; Totiviridae; Tymovirus |
| isometric | Cystoviridae; Geminiviridae |
| oval | Poxviridae |
| pleomorphic | Coronaviridae; Hypoviridae; Plasmaviridae |
| spherical | Arenaviridae; Arterivirus; Bunyaviridae; Flaviviridae; Orthomyxoviridae; Retroviridae; Togaviridae |
| lemon-shaped | Fuselloviridae |
| phages with tail extension | Myoviridae; Podoviridae; Siphoviridae |

One example for such protein shells is shown hereafter on the basis of the Polyomavirus pseudocapsid (protein shell consisting of VP1 subunits of the Polyomavirus). Among the documented examples in previous table 1 for usable viruses and phages, the SSV1 particle (Fuseolloviridae), which infects the Archaebacterium *Sulfolobus shibatae*, has to be stressed. This representative of the phages is hyperthermophilic due of its host specificity, consequently also resistant at high temperatures and due of that it can be also used advantageously for a large number of application in the sectors of the biotechnology and medicine. It can form a very stable protein shell, whereby the building blocks are easy to produce recombinantly. Similar representatives of thermophilic respectively hyperthermophilic phages are found for instance in the Lipothrixviridae, too. Not further classified are the thermophilic and hyperthermophilic representatives of the Bacilloviridae and the Guttaviridae, which can also be used in such processes where the stability of a protein shell (made out of phage proteins) is relevant.

According to the invention monomeric subunits or dimers or oligomers of subunits of the above-mentioned protein shells can be used as protein shell fragments.

Protein shell fragments can be modified in different ways according to the invention, as long as they are still able to assemble with other protein shell fragments to a protein shell.

The first region, with which the protein shell fragments bind to the matrix, can be for example a C-terminal, a N-terminal, or another region of the protein shell fragment, for instance a loop region. Advantageously, the first region is situated in such a way that it lies on the exterior side of the protein shell after the assembly.

The first region can be modified according to the invention in such a way that this first region shows an improved binding affinity to the matrix. These modifications can be, for example, the fusion of a peptide or a peptide domain, which has the known binding properties, to the protein shell fragment with the help of genetic methods. Such a binding-mediating molecule can also be covalently bound chemically, for example, by specific biotinylation after the production of the protein shell fragment. Examples for such modifications in the first region are the fixation of GST (Glutathione-S-Transferase) to glutathion-containing matrices, the use of a His-tag for coupling to nickel-chelate matrices, chitin binding domains in combination with chitin matrices, cellulose binding domains in combination with cellulose matrices, polyionic peptide sequences in combination with oppositely charged matrix surfaces (peptide loaded matrices or typical matrices from the area of ion-exchange chromatography), WW domains respectively SH3 domains in connection with proline-containing matrices, polyproline peptides in combination with matrix-immobilized WW domains or SH3 domains, antigenes in combination with antibody-loaded affinity matrices (for instance from immuno-affinity chromatography), lectins in combination with carbohydrate-loaded matrices, or protein A, protein M, protein G, or protein Z in combination with immobilized antibodies. The binding-mediating molecules can also be connected via linker segments to the protein shell fragments.

The second region of the protein shell fragments, to which molecular substances can bind, can be for example a C-terminal, a N-terminal, or another non-terminally situated region of the protein shell fragment, preferred a loop-region. Advantageously, the second part is located in such a way that after the assembly it is located on the inside of the protein shell.

The second region can, according to the invention, be modified in such a way that this second region shows an improved binding affinity to the molecular substance. These modifications can be, for example, a site-specific mutagenesis of a segment of the protein shell fragment, a fusion with a protein fragment, or the insertion of a protein fragment (protein domain) or a peptide. In the same way, the modification of the protein shell fragment can take place by chemical modification with molecular substances which show a suitable binding affinity as desired. Examples for the modification of the second region are the binding or insertion of substrate analogs for the binding of enzymes, the use of lecitins or lecitin-like domains for the binding of carbohydrates, the use of the bacterial protein A, protein G, protein M, or protein Z for unspecific binding of antibodies, the use of C1 complexes of the complement system for binding of antibodies of specific classes, the binding of antigens for specific binding of antibodies, the use of proline-containing peptides for the binding of WW domains or SH3 domains, the use of SH3 domains or WW domains for the binding of peptides rich in proline, the use of polyionic peptides for binding of peptides or chemical associates (polymers) with the respective opposite charge, the use of oligonucleotides for binding of complementary nucleotide sequences, as for example the use of Poly-T-Tags for binding of the Poly-A-tails of eukaryotic mRNA.

Further, functional modifications in further parts of the protein shell fragment are also possible according to the invention.

The binding of the first region of the protein shell fragment to the matrix can be reversible or irreversible. According to the invention, binding is to be understood in this context as covalent bindings, ionic interactions, van der Waals interactions or other interactions between protein shell fragment and molecular substance. In case of an irreversible binding of the protein shell fragment with the first region to the matrix, after the binding of the molecular substance to the second region of the protein shell fragment, only one region of the protein shell fragment will be separated from the matrix which contains the second region of the protein shell fragment and which can be assembled with other protein shell fragments to a protein shell.

As matrix, according to the invention, every matrix can be used to which protein shell fragments can be bound, for example a chitin matrix, sepharose matrix, dextran matrix or diethylaminoethyle matrix can be used. The matrix can be for instance a solid matrix or it can be present in the form of a gel.

The separation of the protein shell fragments or of the assembled protein shells from the matrix occurs according to known procedures. For example, a linker segment can be separated from the protein shell fragment by a specific, for instance enzymatic cleavage by proteinases, or by activation of an intein. Further possibilities, for example a change of the salt concentration (ionic strength), the pH value, the temperature, or an addition of solvent additives are at one's disposal.

According to one model of the invention one protein shell fragment, for example a capsomer subunit of the polyomavirus VP1 capsid, is reversibly immobilized via the (in this case C-terminal) region of the protein shell fragment to a solid matrix. A specially constituted—in a later example, for instance, a nucleic-acid-binding—segment at the aminoterminal end of the capsomer is not fixed hereby and is freely accessible for the molecular substance which has to be packaged. The capsomer immobilized in this way is now incubated with the nucleic acid which has to be packaged and this binds to the capsomer. Then, the separation of the nucleic acid-loaded capsomer from the matrix follows. Simultaneously or afterwards, the assembly of the nucleic acid-loaded protein component with other capsomers to a virus-like protein shell (capsid) is induced. With this, under suitable, defined molar proportions of loaded and unloaded capsomers, a maximum yield of nucleic acid-containing capsids will be reached. These proportions, for example, can be defined by the expert as follows: There is in each case one experiment carried out in which the concentration of the loaded capsomer is constant, while the concentration of the unloaded capsomers varies. As a measure for the range of variation, the stoichiometry of the capsid can be used, in case of the polyomavirus-hell which consists of 72 capsomers, the variation of the concentration can be for example in the range of 1:71 to 71:1. The evaluation of this experiment should show an optimum curve for the relative quantities of loaded and unloaded capsomeres. If it is required, free subunits of the protein or functional varieties of it can for example be inserted during the assembly. In case of DNA packaging, additionally nucleic acid condensation agents can be used.

In one model of the procedure according to the invention, prior to the packaging of the appropriate molecular substances, for example nucleic acid, into the protein shell of the virus-like capsid, one region of the not yet assembled shell (a protein shell fragment) is immobilized reversibly to a matrix: A second region of the protein shell fragment which has a sufficiently high nucleic acid binding affinity (respectively an adequate affinity to the in the respective case chosen molecular substance) is not fixed and freely accessible for the substance in solution. Then, the molecular substance (for instance a nucleic acid) can be added to the in this way immobilized protein shell fragment (capsomer), for example in the form of a usual circular plasmid which codes for a gene. This nucleic acid binds to the immobilized capsomer via the unfixed nucleic acid binding segment, for example in a stoichiometry of 1:1 (one nucleic acid binding segment per immobilized capsomer). According to the invention, binding is to be understood in this context as covalent binding, ionic interaction, van der Waals bond or other interactions between protein shell fragment and molecular substance. The nucleic acid bound in this way, respectively active agents, are now spatially separated. As a special advantage of the invention the molecular substances cannot interact respectively aggregate with each other due to this spatial separation.

In case of the usage of usual active substances like proteins, peptides, single-stranded and sufficiently short oligonucleotides, etc., the elution step can be immediately performed afterwards. In case of complex and large agents as for example large DNA plasmids, one further step can be necessary. In case of DNA, this is usually the usage of a condensation agent. For example, using histones, histon-like proteins, or adequate polycationic molecules, the condensation of the fixed DNA is induced. The disturbing formation of toroids or aggregates is avoided in this case by spatial separation and indirect binding of the nucleic acid molecules to the matrix.

For condensation of DNA, using it as a molecular substance which has to be packaged using the procedure according to the invention, any condensation agent can be used in general, so for example histones, histone-like proteins, polycations, polyarginine, polylysin, spermidine, methylized spermidine, CTAB (cetyl trimethyl ammonium bromide), cationic lipids, lipospermine, polyethylene glycol, polyethylene imin, cobalt-amine-compounds or manganese-compounds.

From simple experiments the expert can find out if the condensation agent competes with the binding of the nucleic acid to the capsomer and due of this the nucleic acid is prematurely separated from the capsomer. Analogously, this applies to all active agents that can be used.

The complete protein shell subsequently can be completely assembled around the active agent respectively the condensed nucleic acid, whereby the bound capsomer is the initiation-building-block and defined amounts of free capsomers (or variations of it) are added. The assembly optionally can already be done during the elution, consequently still in the direct environment of the matrix, or after the release of the complex consisting of capsomer and active agent and separation from the matrix. For some processes, an assembly at the matrix, still prior to the release of the capsomers, can be advantageous; this is also possible by usage according to the invention.

The capsomer can be arranged in such a way that at an interior part of the capsomer (for example the N-terminal region when using the protein PyVP1 as capsomer) a high affinity nucleic acid-binding segment is located. This can be the natural N-terminal end of the wild type protein in case of PyVP1 which has known nucleic acid-binding properties. In other viral envelopes or phage coats this can be the C-terminal end or a loop structure on the inside of a capsid, too, which can be recognized on the basis of the tertiary structure of the coat proteins. Of advantage is the use of modified segments which bind with unusual high affinity to DNA or specific other nucleic acid types. One example for this are the well analysed protamine-related sequences from the capsid protein of the hepatitis B virus p21.5 which show DNA and RNA binding properties (cf. T. Hatton, S. Zhou & D. N. Standring, "RNA- and DNA-binding activities in Hepatitis virus capsid protein: a model for their roles in viral replication", J. Virology 66, S. 5232–5241, 1992). In the following, examples according to this are a series of N-terminally modified capsomeres are described which show such high affinity binding segments. However, the usage according to the invention should not be restricted to these examples. Rather, many other high affinity binding segments can be inserted within the usage according to the invention. For the binding of other active agents, the respective method can be used; proteins and peptides can be bound by using affinity binding partners to the capsomere structure, as it is demonstrated in the following examples. Examples for this are the avidin-biotin interaction, the interaction of WW domains respectively of SH3 domains with peptide sequences rich in proline, the interaction of oppositely charged polyionic sequences, etc.

For the invention, the use of an intein-based fusion construct in the described procedure can be used with special advantage. Here, the separation of the immobilized complexes from the matrix by change of the redox conditions in the solution takes place, for example by simple addition of Dithiothreitol (DTT) or hydroxylamine, consequently by cleavage of a covalent binding. These redox conditions can be changed easily without the presence of loaded capsomers or active substances like DNA or other nucleic acids having a negative effect on it.

Especially advantageous according to the invention is the use of an oligomer capsomer, since the binding of an oligomer to the matrix is much stronger (due to cooperative effects) than the one of single monomers.

Furthermore, the procedure offers the advantage that at the immobilized part (preferably a capsomer from a protein shell) allows a screening for optimization of the packaging properties of the system. Such a screening can lead among others to improvements of the physicochemical or solvent conditions, the DNA sequence, or the molecular binding module, which are used in the packaging procedure. Furthermore, the properties of the molecular substance as for instance its maximum size permitted for the packaging can be analysed. Such a limit in size is especially of importance for the enclosure of DNA in virus-like vector systems. The elucidation of the limit can simply occur in such a way that a heterogeneous DNA population with respect to the size of the fragments is added to the immobilized capsomer. These heterogeneous fragments can be produced enzymatically, by use of restriction enzymes or by fractions of large DNA molecules. After the usage of the described procedure according to the invention and after benzonase digestion of the DNA not packaged or peripherally attached, the packed DNA protected in the virus-like particle is analyzed on an agarose gel. The largest DNA still packed into particle marks the limit in size which can be packaged with this procedure using the respective protein shell.

An essential advantage of the procedure is that the protein shell fragment bound to the matrix can be of different chemical or physical nature than the other building blocks used for protein shell formation. This has the special advantage that a mixed assembly of the protein shell is possible. The immobilized part has the specific function of binding and internalization of the molecular substance to be packed. Further functions for the production of a vector system with nearly any properties can be anchored in the other regions of the protein shell. The mosaic-like mixed assembly thus permits the generation of heterogeneous particles, whereby the directed insertion of a substance in the inner cavity can be guaranteed by the immobilized part.

Finally, the immobilized protein region or the molecular substance to be packed can be labelled with, for instance, a fluorescent or radioactive molecule, a specific binding peptide segment (tagging), a biotinylation or other chemical labelling, or even on another way and with this—after the assembly to virus analogous protein shells—it can be identified afterwards. This has the special advantage that with this a determination of the specific packaging efficiency by analysis of the assembled protein shell is possible, the produced protein shells which have a label contain the capsomer as a part of the shell which is responsible for the packaging of the molecular substance and consequently, with the choice of suitable conditions, with high probability also the molecular substance itself. In contrast, empty protein shells, that means shells which have formed spontaneously in the solution from the remaining parts of the protein shell subunits added and which exclude the molecular substance which has to be packed, and loaded shells can be distinguished. With this special labelling (if necessary also in combination with a special binding segment or a biotinylation), a selection of protein shells loaded with the molecular substance from empty protein shells is possible, and with that the production of homogeneous populations of virus-like protein shells with packaged molecular substance in each case.

The following examples show models of the present invention without limiting the protection of it.

The examples and the description refer to the following figures:

FIG. 1 shows schematically and as an example a model of the invention. One capsomer from a viral envelope (protein shell fragment) is immobilized reversibly with a first region to the matrix and brought into contact with the molecular substance which has to be packed, which binds to a second region of the capsomer ("lying on the inside", affine structure). The loaded protein shell fragment is separated from the matrix and the assembly/accumulation with free capsomeres to the virus-like particle is induced. With this, a directed packaging of the molecular substance into the inside of the particle can be achieved.

FIG. 2 shows elution profiles of nucleic acid (plasmid pEGFP-N1), which have been bound to immobilized capsomers of VP1 (FIG. 2a), respectively 234-VP1 (FIG. 2b) before and have been separated by a linear salt gradient between 100 and 2000 mM NaCl from the capsomers. The elution of the nucleic acid of PyVP1-wildtype takes place at 810 mM NaCl, the one of 234-PyVP1 takes place at 970 mM NaCl. Therefore, 234-PyVP1 can bind DNA much stronger than wildtype-PyVP1.

FIG. 3 shows a SDS gel electrophoretic analysis (12% gel) of the protein content of different fractions after separation of the loaded capsomers, assembly to capsids, and elution of the loaded capsids from the chitin matrix. The lane M mark the molecular mass standard, respectively; the running position of the PyVP1 protein is marked, respectively. Lanes 1 to 14 (respectively 13) contain different elution fractions of the experiment.

FIG. 4 shows the analysis of the nucleic acid loading of the capsid fractions on 1% agarose gel, stained with ethidium bromide. In both FIG. 4a (PyVP1) and FIG. 4b (234-PyVP1), lane M marks the size standard for nucleic acid; lanes 1 to 14 (respectively 13) are elution fractions after the extraction of the DNA by means of standard protocols, respectively (the numerical order of the lanes is identical to FIG. 3). DNA is mainly contained in the same fractions where according to FIG. 3 capsid protein is contained, too, that means that the DNA coelutes together with the capsid. The 234-PyVP1-variation, as an advantage over the PyVP1-wildtype protein, has packaged a larger amount of nucleic acid, obviously due to the stronger DNA binding of the N-terminally added protamine-like sequence.

FIG. 5 shows the analysis of the packaging efficiency of capsids by digestion of unprotected DNA using benzonase. To 400 µl of capsomeres formed after two days after matrix packaging and assembly from PyPV1 and 234-PyVP1, 2 µl benzonase and 4 µl $MgCl_2$ (1 M) are added, respectively, and this mixture is incubated for 1 h at 37° C. Then, the extracted nucleic acid is loaded on an agarose gel (1%) and stained with ethidium bromide. The upper lanes of the figure show an untreated test sample; the last lanes shows the samples which are treated with benzonase. Fraction 6 to 9 of PyVP1-capsids as well as 6 to 13 of 234-PyVP1 are loaded (cf. FIGS. 3 and 4). The PyPV1-capsid shows a small protection against digestion, the 234-PyPV-capsids show a distinct protection against nuclease digestion even under the chosen stringent conditions, especially in the fractions 6 to 8.

EXAMPLE 1

Production of PyPV1-Capsomers with Intein/CBD-Fusion Moiety for Immobilization to a Chitin-Matrix The expression and purification of PyVP1 occurs as fusion protein with a C-terminally fused intein domain and a chitin binding domain (CBD) added to it. For that purpose, a plasmid is generated which is based on the commercially available vector pCYB2 of the IMPACT-system (company: New England Biolabs). Via the multiple cloning site of the pCYB2 by the restriction sites NdeI—XmaI a DNA-fragment produced by PCR amplification and in regard to this digested with the same restriction enzymes is cloned which codes for the VP1 gene of the mouse polyomavirus. As basis for this, the polyomavirus variant is used which does not show any cysteine in the sequence; the six cysteine of the wildtype protein have been replaced before by serine. This variation of PyVP1 has the advantage that the redox conditions of the solution have no influence on the condition of the protein, and by that it is easier to handle in many applications. For the purpose of labelling, a new cysteine instead of a threonine is introduced into the protein at the position 249 which makes, for example, a specific labelling possible with fluorescent dyes; the variant used is thus called PyVP1-CallS-T249C or short PyVP1 in the following. For the PCR, the following oligonucleotides are used as primers: 5'-TAT ACA TAT GGC CCC CAA AAG AAA AAG C-3' (SEQ ID NO:11), and 5'-ATA TCC CGG GAG GAA ATA CAG TCT TTG TTT TTC c-3' (SEQ ID NO:12). In this PCR simultaneously the C-terminal amino acids of the wildtype-VP1-protein are transformed from Gly383-Asn384 into Pro383-Gly384, since a C-terminal asparagine is very disadvantageous for the intein cleavage system. The named point mutation does not influence the essential properties of the PyVP1 protein in the following. The tac-promoter of the pCYB2-vectors yields only a small amount of expression of the fusion protein, therefore the fusion construct PyVP1-intein-CBD is isolated by a further PCR from the pCYB2-vector and cloned into a highly expressing pET-vector with a T7lac-promoter (pET21a, Company: Novagen), via NdeI—EcoRI—restriction sites. Oligonucleotides: 5'-TAT ACA TAT GGC CCC CAA AAG AAA AAG C-3' (SEQ ID NO:13), and 5'-ATA TGA ATT CCA GTC ATT GAA GCT GCC ACA AGG-3' (SEQ ID NO:14).

The created vector permits the expression of the fusion protein PyVP1-intein-CBD with the help of the high-expressing T7lac-promoter in *E. coli* BL21(DE3)-cells (company: Novagen). For this, the transformed cells are cultivated in 5 1 Erlenmeyer flasks, each containing 2 1 LB-medium, at 37° C., until $OD_{600}$ of the culture is between 2.0 to 2.5. For induction of the protein expression, IPTG is added up to a final concentration of 1 mM. The cultures are incubated for protein expression for further 20 hours at 15° C.; the low temperature prevents the intein part of the fusion protein from cleavage under in vivo-conditions. Then, the cells are harvested by centrifugation, solved in 70 ml resuspension buffer (20 mM HEPES, 1 mM EDTA, 100 mM NaCl, 5% (w/v) glycerol, pH 8.0) and lysed by high pressure homogenization. After centrifugation of the crude extract for 60 min at 48 000 g, a clear cell extract is obtained. It is immediately loaded on a 10 ml chitin-affinity matrix (New England Biolabs) with a flow rate of 0.5 ml/min at 10° C. Then, the column is washed with 3 column volumes of the resuspension buffer, 15 column volumes of a washing buffer with high ionic strength (20 mM HEPES, 1 mM EDTA, 2 M NaCl, 5% (w/v) glycerol, pH 8.0) and again with 3 column volumes of the resuspension buffer; by which all undesired *E. coli*-host proteins are removed from the chitin matrix.

At this stage of the experiment the PyVP1-protein is immobilized by the intein fusion part and the chitin-binding-domain (CBD) to the chitin matrix with high affinity and cannot be eluted from the matrix even by buffers of high ionic strength, for instance the previously mentioned washing buffer with 2 M NaCl. It turned out to be advantageous that the PyVP1 protein is a pentamer in solution which is consequently fixed as fusion protein PyVP1-intein-CBD with 5 binding moieties with high affinity to the chitin matrix. This part of the fusion does not disturb the pentamerization of the protein, but it prevents the premature assembly of the pentamers to capsids, for which a free C-terminal end of the protein is essential. Under the previously described fixed conditions, the loading of the PyVP1-pentamer via the free N-terminal end can take place (cf. the following examples 2 and 3).

Using a pulse (3 column volumes) with 50 mM dithiothreitol (DTT), 50 mM hydroxylamine, or 30 mM DTT with 30 mM hydroxylamine, respectively, in the resuspension buffer, the cleavage of the PyVP1 capsomer from the fusion protein by the self-splicing intein activity can be induced. For that purpose a loaded chitin matrix with one of the solutions mentioned is incubated at 10° C. for 14 hours. The PyVP1 is completely set free and can be eluted and separated from the chitin matrix and the other matrix-bound components of the fusion protein by column-chromatographic procedures. For this, a linear salt gradient with a concentration between 0.1 and 2.0 M NaCl is used appropriately. The regeneration of the chitin matrix takes place according to the recommendation of the manufacturer by washing of the chitin material with 3 column volumes of a SDS containing buffer (1% SDS (w/v) in resuspension buffer) at room temperature.

EXAMPLE 2

Binding of Plasmid DNA to a Matrix-Immobilized PyVP1 Coat Protein

It is known that PyVP1 after recombined expression, in which it is present as pentamer protein, can be assembled in vitro to a virus-like protein shell.

The association of heterologous DNA to the protein shell has been also shown by measuring the protection of the DNA against nuclease digestion. This happened of course with only little yield. Above this, a size limit of approximately 1 to 2 kbp length of protected DNA is observed.

It is supposed that the N-terminus of the PyVP1 protein shows nucleic acid binding properties. These natural binding properties are possibly not sufficient for some applications. For that reason, alternatively to the application of the wildtype-PyVP1, a strong DNA-binding peptide sequence which is derived from the DNA binding region of the capsid protein p21.5 of the hepatitis B virus (so called repeats II, III and IV; in the following termed as 234-sequence) is fused by gene technological methods to a PyVP1 shortened by 18 amino acids at the N-teminus. Therefore, a synthetic double-stranded 78-bp-oligonucleotide of the sequence 5'-ATG GCC AGC CCG CGT CGT CGT ACC CCA AGC CCA CGT CGT CGT CGT AGC CAG AGC CCG CGG TCG TCC GGT CGT AGC CAG-3' (SEQ ID NO:15) is synthesized and inserted into the expression vector from example 1 using standard cloning procedures; with that, the first amino acids of the PyVP1 protein (sequence: MAPKRKSGVS KSETKSTK; SEQ ID NO:16) are replaced by the 234 sequence (coded sequence of the 78-bp-oligonucleotides; sequence: MASPRRRTPS PRRRRSQSPR RRRSQ; SEQ ID NO:17). The production of the 234-PyVP1 protein is analogous to the conditions described in example 1. Surprisingly, the stable and defined binding of a plasmid-DNA (pEGFP-N1, company: Clontech) to a 234-PyVP1 immobilized in this manner succeeded.

In the standard buffer with low ionic strength (20 mM HEPES, pH 8.0, 100 mM NaCl, 1 mM EDTA) the DNA does not bind to the chitin matrix and occurs in the flow-through after it is loaded on a chromographic column containing the chitin material. The loading of the chitin matrix with 234-PyVP1 is carried out according to the conditions from example 1. After washing of the column with a buffer of high ionic strength (standard buffer, see above, with a total of 2.0 M NaCl), the column is equilibrated again with the standard buffer. Then, 30 μg of the plasmid are injected. This corresponds to 10 pmol of the plasmid used; at a protein amount of 2–4 mg (10–20 nmol 234-PyVP1-pentamers) on the matrix, the plasmid is in an approximately thousand times molar shortage. The DNA completely binds to the immobilized 234-PyVP1-capsomeres under these conditions. An identical experiment can be carried out using the wildtype-PyVP1 and results in analogous yields.

For analysis the DNA can afterwards be eluted again with a linear NaCl gradient between 0.1 and 2.0 NaCl (cf. FIG.

2). The elution maximum of the DNA lies at a salt concentration of 810 mM in the case of the PyVP1, in comparison to that it is at a salt concentration of 970 mM NaCl when using the modified protein 234-PyVP1, that means a stronger binding occurs than with the wild type-protein. This experiment demonstrates that the DNA binding property of the wildtype PyVP1 and of the 234-PyVP1 is preserved if they are produced as a fusion construct according to the previous description, respectively, and immobilized to a solid matrix. At the same time it is shown that with the choice of an adequate affine binding site at the N-terminus of VP1, the binding properties of the molecular substance which has to be packed can be modulated.

Analogous to the described example, a RNA-binding sequence can be used. For that purpose the first repeat of this binding region (repeat 1) is used instead of the termed 234-sequence of the DNA-binding region of the capsid protein p21.5 of the hepatitis B virus, which is repetitively used one after the other in three copies (111-sequence; sequence: MARRRDRGRS RRRDRGRSRR RDRGRS; SEQ ID NO:18) and again replaces the first N-terminal amino acids of the wildtype-PyVP1-protein. For this, the synthetic, double-stranded oligonucleotide of the sequence 5'-ATG GCG CGT CGT CGT GAT CGT GGC CGT AGC CGT CGT CGT GAT CGT GGT CGT AGC CGT CGT CGT GAT CGT GGT CGT AGC-3' (SEQ ID NO:19) is cloned into the corresponding expression vector by standard methods and the resulting 111-PyVP1-protein is produced in analogy to example 1. The repetitive sequence of the N-terminus binds RNA with high affinity. The 111-PyVP1-protein produced in the same manner as the 234-PyVP1 shows analogous properties to the 234-PyVP1 with the exception that specifically RNA instead of DNA can be packed as nucleic acid.

EXAMPLE 3

Co-Elution of DNA and VP1 after Cleavage from the Intein Fusion Moiety

After the nucleic acid is loaded on and it is completely bound to the immobilized capsomers, the cleavage buffer is added to the mixture described in example 2 (using 234-PyVP1) which induces the removal of the capsomer from the fusion moiety. The cleavage buffer contains the components of the standard buffer, and additionally 50 mM DTT or 50 mM hydroxylamine (cf. example 1) for separation of the intein fusion construct according to the recommendations of the manufacturer (company: New England Biolabs), the condensation agent cetyl trimethyl ammonium bromide (CTAB) in a concentration of 20 μM, and 0.5 mM $CaCl_2$ for the induction of the assembly of the protein shell of the virus-like capsid from the capsomeres. After incubation of the mixture on the column at 15° C. overnight it is eluted by a linear NaCl gradient and the separated fractions are analyzed in three ways:

- protein: a SDS-polyacrylamide gel stained with Coomassie is used for the proof of the eluted protein, that means of the released capsomers (cf. FIG. 3)
- nucleic acid: After phenol-chloroform extraction and ethanol precipitation of the DNA the DNA-content of the fraction is determined in a gel stained with ethidium bromide (cf. FIG. 4)
- protected (packed) nucleic acid: After benzonase digestion (company: Merck, 10 units in 400 μl), which is stopped by the addition of 0.5% SDS and 20 mM EDTA and the following phenol-chloroform extraction and ethanol precipitation, the portion of the DNA which is protected against benzonase activity (that means taken into the inside of the assembled protein shell) is defined. This occurs by analysis on an agarose gel stained with ethidium bromide (cf. FIG. 5).

The evaluation of the experiment as well as FIGS. 3 to 5 show that a coelution of the DNA with the protein takes place, that means the DNA added binds stably to the immobilized capsomeres. During the cleavage and in the course of the establishing of the linear salt gradient for elution of the complexes, binding between the capsomer and the DNA stays preserved. Furthermore, an important protection of the DNA against digestion by nuclease is shown in most of the fractions. This protection extends to the completely original plasmid size, that means the plasmid is completely packaged into the capsid, respectively, and with that protected against digestion by nuclease (benzonase). In the example shown the efficiency in the case of the 234-PyVP1-capsid under suitable conditions is about 20% of the DNA amount used. In packaging experiments without matrix immobilization according to the standard procedure of the osmotic shock, maximum efficiencies in the range of 2–4% have been observed. With that, the procedure described is suitable for the directed packaging of molecular substances, as for instance nucleic acids, into the inside of a protein shell.

EXAMPLE 4

Transfection of Matrix-Packaged DNA in Eukaryotic Cells

The system described in example 3 is used for gene transfer of plasmid pEGFP-N1 into NIH3T3 cells. The capsids fractionated after elution from the column are added for that purpose in the presence of benzonase (5 units) for digestion of free plasmid DNA still present to the NIH3T3 cells which are seeded the day before (20 000 cells and 40 μg complex per experiment). After 48 h incubation of the cells at 37° C. and 5% $CO_2$ the cells are washed three times with PBS, incubated with trypsin/EDTA-solution for 5 min, and then loosened from the bottom. Upon the expression of the eGFP gene the green fluorescent protein GFP is produced whose fluorescence can be measured in the fluorescence activated cell sorter (FACS). An analysis of the transfected cells by FACS shows the total amount of GFP fluorescence which is 170% of the basic fluorescence of cells not transfected. With this it is shown that the virus-like capsids produced according to example 1 and 3 at the matrix are able to efficiently transport molecular substances, as for instance nucleic acid, into cells. The components used are not toxic; in the cells the nucleic acid can be brought to expression. Therefore, a productive gene transfer takes place by the system used.

EXAMPLE 5

Packaging of Peptides, Proteins or Pharmaceutical Agents

Apart from the use of nucleic acids described in examples 2 and 4, also a directed packaging of other active agents, for example proteins or peptides, can take place. For that purpose, a binding site at the inside of the capsomer is modified in such a way that a fixation of the protein or peptide agent by an affinity binding to this binding site takes place.

This fixation can take place for example by ionic interactions, that means by two oppositely charged peptide parts, or by a binding with hydrogen bonds between the capsomer on its inside and the peptide or protein. Finally, even natural, known interactions like the one between SH3 domain and sequences rich in proline or the one between the protein avidin and the peptide sequence known as strep-tag can be used. For that purpose, one binding partner is provided during the production with an adequate binding segment, the active substance to be packed analogous to tis with a complementary binding segment. The fixation of the binding segments with recombinant production of the capsomer with the help of gene technological standard methods can occur especially simple when peptides, proteins or protein domains are used as binding segments. These binding segments can be produced according to standard procedures. In the same manner this is valid for the active substance to be packed with the complementary binding segment located on it. After immobilization of the capsomer to the matrix and the fixation of the peptide or protein under arrangement of the two complementary binding segments, again the steps of separation from the matrix and assembly of the capsomers to the protein shell take place, whereby the order of the two steps can vary according to the process. In this manner in analogy to the previously described nucleic acid packaging the directed packaging of other active substances, as for instance proteins or peptides, can be carried out, too.

EXAMPLE 6

Packaging of GFP (Green Fluorescent Protein)

In this example it is shown that by advantageous placing of adaptor segments a directing of the molecular substances, in this case proteins, into the inside of viral envelopes or virus-like coats (capsids) can take place with the help of the matrix-supported procedure. In consideration of the three-dimensional structure of polyomavirus VP1 it is known according to the state of the technology that the N-terminus of the protein is located at the inside of the shell after the assembly to a capsid. Consequently, a variant of the PyVP1 protein is produced which contains so called WW-domains at the amino-terminus of the native wildtype protein (variation PyVP1-WW1). The basis for this variation is as in example 1 a VP1 protein of the polyomavirus which has replaced all natural cysteines by serines and in which a new cysteine is additionally inserted (PyVP1-CallS-T249C, shortened PyVP1). WW domains are small protein domains which have a high affinity to proline-rich sequences; the WW-domain of the sequence Gly-Ser-Gly-Trp-Thr-Glu-His-Lys-Ser-Pro-Asp-Gly-Arg-Thr-Tyr-Tyr-Tyr-Asn-Thr-Glu-Thr-Lys-Gln-Ser-Thr-Trp-Glu-Lys-Pro-Asp-Asp-Asp-Asp-Asp-Asp-Asp (SEQ ID NO:20) (from the FBP11-gene product of the mouse) shows especially high affinity to the peptide sequence Pro-Pro-Leu-Pro (SEQ ID NO:21).

In first instance an amplification of a WW-domain is carried out by PCR; the FBP11-gene of the mouse serves as template. As oligonucleotides for the PCR 5'-AAT ATA TCA TAT GTC CAT CAT CCG GCT TTT CCC AGG TAG ACT-3' (SEQ ID NO:22) (with NdeI-restriction site), and 5'-TAT TAA TCA TAT GAG CGG CTG GAC AGA ACA TAA ATC ACC TGA TGG-3' (SEQ ID NO:23) are used. The PCR-product obtained with that is afterwards cloned by the restriction sites Nde I—Nde I inserted by the oligonucleotides into the expression vector pET21 a from example 1 which contains the gene for a fusion protein PyVP1-intein-CBD; at the 5'-end of the gene a singular Nde I restriction site is located. The expressed gene product of this vector is the desired protein PyVP1-WW1. The expression and purification of the protein takes place in accordance with example 1. Here, as in example 1 the protein is immobilized to the chitin matrix and the components not bound are removed by the washing solution.

In analogous manner, the production and purification of a GFP variant is performed. GFP is a protein which shows under native condition a green fluorescence (absorption maximum at 490 nm). Consequently, it is excellently suitable for labelling of complexes and associations.

For production of a GFP variant with a terminal sequence rich in proline first a PCR-based amplification of the GFP gene takes place, whereby the template of the plasmid pEGFP-N1 (company: Clontech) is used. Contemporary suitable restriction sites are inserted into the PCR product. The PCR takes place with the oligonucleotides 5'-TTA TTT ACA TAT GGT GAG CAA GGG CGA GGA G-3' (SEQ ID NO:24) (with NdeI-restriction site), and 5'-ATA TCT TAA GTA CAG CTC GTC CAT GCC G-3' (SEQ ID NO:25) (with AflII-restriction site). The PCR-product obtained in this way is cloned by the restriction sites into the vector pTIP and is expressed there; this vector is a derivative of the documented intein-cleaning vector from example 1 basing on pET21 a with additionally inserted sequences rich in proline. The vector is constructed in such a way that optionally at the 5'- or 3'-end of a gene inserted by a multiple cloning site, a sequence rich in proline is fused. The sequence rich in proline contains mainly Pro-Pro-Pro-Pro-Pro-Pro-Pro-Pro-Leu-Pro (SEQ ID NO:26), and with that the strongly binding sequence rich in proline which is necessary for the fixing to the WW domain. The production and purification of the GFP-PPLP protein takes place by chitin affinity chromatography in agreement with the example 1. The GFP-PPLP-protein, which has on the C-terminus the sequence rich in proline Pro-Pro-Pro-Pro-Pro-Pro-Pro-Pro-Leu-Pro (SEQ ID NO:26), can be solubly produced in large amounts. The green colour of the protein solution shows at the same time that the protein can fold to its native structure.

The PyVP1-WW1-protein which is immobilized on the chitin column is at first incubated with the GFP-PPLP (in the molar relation 1:6) on the matrix for 20 min (solvent: 10 mM HEPES, 1 mM EDTA, 150 mM NaCl, 5% glycerol, pH 7.2). Then, the cleavage of the PyVP1-WW1-fusion protein from the intein domain is induced by addition of reducing agents according to example 1. The PyVP1-WW1-protein is eluted together with the GFP-protein bound via WW-polyproline-affinity from the column and immediately afterwards a solution is added with unmodified PyVP1-proteins in the stoichiometric relation of 1:1 to 1:10. The capsid formation of the PYVP1 variants is induced by dialysis against a buffer which contains 0.5 mM $CaCl_2$. On the basis of gel filtration examinations (column TSKGel G6000PWXL, company: TosoHaas) it can be shown that a part of the native GFP-PPLP-protein (which can be identified on the basis of the specific absorption at 490 nm) is included in the capsid fraction (at elution volumes between 9 and 10 ml). This means that during the incubation of the GFP-PPLP-protein with the matrix-associated variant PyVP-WW1 on the column a binding of both proteins to each other took place, by which the GFP has been directed into the inside of the virus-like particle at the following capsid assembly.

In summary, the experiment in this example shows that variants of PyVP1 with the WW-domain fusioned N-terminally to it are able to bind sequences rich in proline under matrix-associated conditions and to direct these as well as the molecular substances connected to it during assembly into capsids under suitable conditions into the inside of virus-like shells. With that, the procedure described is suitable to cause a directed packaging of molecular substances into viruses respectively virus-like capsids. An essential advantage which has to be mentioned over the packaging in solution is the avoidance of aggregation of the substance which has to be packed, which can be used in sufficiently little concentration. By immobilization after binding to the matrix-bound PyVP1-WW1 protein the aggregation can be completely avoided and the molecular substance is concentrated on the column without aggregation coming into action.

EXAMPLE 7

Loading over Biotin/Avidin (Streptavidin)—Interaction

A further case of application is the use of the widespread system for production of interactions also on basis of avidin (or streptavidin respectively other derivatives) with biotin. This interaction is extraordinarily strong; molecules that interact with each other via this interaction are almost inseparably bound to each other. This property is often used for coupling of biomolecules. A disadvantage of the system is that avidin has a total of four binding sites for biotin. The simple incubation of biotinylated substances with avidin often leads to the undesired formation of (homo-)tetramers in solution or to formation of aggregates. Within the present invention this disadvantage according to the state of the available technology can be removed by matrix immobilization. For that—as in the previous examples shown—for example a modified viral coat protein is used which has one singular cysteine on one exposed site (in example 1 PyVP1-CallS-T249C, compare sequence protocol). This coat protein, as described in the previous examples, can be immobilized to a matrix. Afterwards, a reagent is added which has on one side a reactive maleimide group and on the other site a functional group like for example biotin; both these groups are separated by a suitably long spacer. Such reagents are commercially available, for example from the company Pierce. If this reagent is incubated with the immobilized PyVP1-CallS-T249C the maleimid group forms a stable and specific covalent bond with the singular cysteine of the PyVP1-CallS-T249C. In the following, avidin respectively streptavidin can be added which binds with high affinity to the biotin group. Afterwards, the capsomers can be separated according to the procedure described in example 1, and one obtains capsomers which carry avidin respectively strepavidin. These can be incubated before or after separation from the matrix with a further biotinylated substance by which one receives capsomers which are bound stably by the biotin-avidin-biotin-interaction to the molecular substance, which for example can be packaged in the inside of the capsids. By the described matrix-protected procedure it is avoided that aggregate formation or premature formation of homotetramers takes place and an uniform loading of the capsomers is induced.

The invention claimed is:

1. Method for the inclusion of molecular substances selected from the group consisting of single-stranded DNA, double-stranded DNA, single-stranded RNA, double-stranded RNA, peptides, peptide hormones, proteins, protein domains, glycoproteins, ribozymes, PNA (Peptide Nucleic Acid), pharmaceutical substances, nucleotides, hormones, lipids, carbohydrates, and combinations of one or more of these substances, in protein shells, said method comprising:
fixation of a protein shell fragment of a polyomavirus with a first region to a matrix on which protein shell fragments can be bound;
bringing the matrix-bound protein shell fragment in contact with the molecular substance, in order to fix the molecular substance to a second region of the protein shell fragment;
separation of the protein shell fragment with the bound molecular substance, or of one part of the protein shell fragment which contains the bound molecular substance, from the matrix;
and
assembly of the separated protein shell fragment or a part of it which contains the bound molecular substance, with other protein shell fragments to a protein shell, whereby the separation and the assembly can be done in any order.

2. Method according to claim 1, wherein the separation and the assembly occur simultaneously, or first the assembly and then the separation occurs.

3. Method according to claim 1, wherein after bringing the matrix-bound protein shell fragment in contact with the molecular substance, one or more condensation agents is added, in order to reach a more compact structure of the molecular substances.

4. Method according to claim 3, wherein histones, histone-like proteins, polycations, polyarginine, polylysin, spermidine, methylized spermidine, CTAB (Cetyltrimethyl-ammonium-bromide), cationic lipids, lipospermine, polyethylene glycol, polyethylene imine, cobalt-amine-compounds or a combination of one or more of these substances are used as condensation agents.

5. Method according to claim 1, wherein the molecular substance is DNA in the form of linear or circular plasmids, single-stranded or double-stranded oligonucleotides, chromosomes or chromosome fragments, or
RNA in the form of antisense-RNA, ribozymes, catalytic RNA, or coding mRNA,
or
as molecular substances proteins in the form of antibodies, single-chain antibodies, enzymes, structure proteins, or marker proteins, are used.

6. Method according to claim 1, wherein the protein shell is a virus capsid of a polyomavirus.

7. Method according to claim 1, wherein the protein shell consists of identical protein shell fragments.

8. Method according to claim 1, wherein the protein shell fragments are monomeric subunits or dimers or oligomers of subunits of a virus capsid of a polyomavirus.

9. Method according to claim 1, wherein the protein shell fragment in the first region is modified in such a way that this first region has an improved binding affinity to the matrix.

10. Method according to claim 1, wherein the first region lies at the C-terminal part of the protein shell fragment and the second region at the N-terminal part, or the first region lies at the N-terminal part and the second region at the N-terminal region.

11. Method according to claim 1, wherein the binding of the protein shell fragment to the matrix with the first region is reversible.

12. Method according to claim 1, wherein an irreversible binding of the protein shell fragment to the matrix occurs via the first region and after the binding of the molecular substance to a second region of the protein shell fragment only the part of the protein shell fragment is separated which contains the second region of the protein shell fragment, and which can be assembled with other protein shell fragments to a protein shell.

13. Method according to claim 1, wherein a label is attached to the protein shell fragment in a third region and/or to the molecular substance.

14. Method according to claim 13, wherein the label is a fluorescent or radioactive molecule, a specifically binding peptide segment, or a biotin.

15. Method according to claim 1, wherein the matrix is a chitin matrix, sepharose matrix, dextrane matrix, or diethylaminoethyl matrix.

16. Method according to claim 1, wherein the matrix is in solid form or a gel.

17. Method according to claim 10, wherein the modification of the first region occurs by insertion of an intein domain in combination with a matrix binding domain, by specific biotinylation, or by appending of a molecule which mediates binding, and/or that the modification of the second region occurs by fusion with a peptide or protein which has a high affinity for the molecular substances to be packaged.

18. Matrix with a protein shell fragment of a polyomavirus which is assembled and is bound to the matrix, wherein a substance, selected from the group consisting of single-stranded or double-stranded DNA, single-stranded or double-stranded RNA, peptides, peptide hormones, proteins, protein domains, glycoproteins, ribozymes, PNA (Peptide Nucleic Acid), pharmaceutical substances, nucleotides, hormones, lipids, carbohydrates and a combination thereof is bound to the protein shell fragment and the protein shell fragment with the bound molecular substance can be at least partially removed from the matrix.

19. Matrix according to claim 18, wherein the protein shell fragment is associated with further protein shell fragments.

20. Method of claim 1, wherein the protein shell consists of protein shell fragments varying from each other.

21. Method of claim 9, wherein the protein shell fragment is modified in the second region in such a way that this second region shows an improved binding affinity to the molecular substance.

22. Method of claim 1, wherein the first and second regions lie outside of the C-terminal part and the N-terminal part of the protein shell fragment.

23. Method of claim 22, wherein the first and second regions lie in loop regions of the protein shell fragment.

* * * * *

SEQUENCE LISTING

```
<160> NUMBER OF SEQ ID NOS: 26

<210> SEQ ID NO 1
<211> LENGTH: 1152
<212> TYPE: DNA
<213> ORGANISM: Artificial Sequence
<220> FEATURE:
<223> OTHER INFORMATION: Description of Artificial Sequence:polyomavirus
      VP1 gene with exchange of all Cys to Ser and
      exchange of Thr 249 to Cys (PyVP1-CallS-T249C)
<220> FEATURE:
<221> NAME/KEY: CDS
<222> LOCATION: (1)..(1152)
<223> OTHER INFORMATION: PyVP1-CallS-T249C

<400> SEQUENCE: 1 atg gcc ccc aaa aga aaa agc ggc gtc tct aaa agc gag aca aaa agc       48
Met Ala Pro Lys Arg Lys Ser Gly Val Ser Lys Ser Glu Thr Lys Ser
  1               5                  10                  15 aca aag gct agc cca aga ccc gca ccc gtt ccc aaa ctg ctt att aaa       96
Thr Lys Ala Ser Pro Arg Pro Ala Pro Val Pro Lys Leu Leu Ile Lys
             20                  25                  30 ggg ggt atg gag gtg ctg gac ctt gtg aca ggg cca gac agt gtg aca      144
Gly Gly Met Glu Val Leu Asp Leu Val Thr Gly Pro Asp Ser Val Thr
         35                  40                  45 gaa ata gaa gct ttt ctg aac ccc aga atg ggg cag cca ccc acc cct      192
Glu Ile Glu Ala Phe Leu Asn Pro Arg Met Gly Gln Pro Pro Thr Pro
     50                  55                  60 gaa agc cta aca gag gga ggg caa tac tat ggt tgg agc aga ggg att      240
Glu Ser Leu Thr Glu Gly Gly Gln Tyr Tyr Gly Trp Ser Arg Gly Ile
 65                  70                  75                  80 aat ttg gct aca tca gat aca gag gat tcc cca gga aat aat aca ctt      288
Asn Leu Ala Thr Ser Asp Thr Glu Asp Ser Pro Gly Asn Asn Thr Leu
                 85                  90                  95 ccc aca tgg agt atg gca aag ctc cag ctt ccc atg ctc aat gag gac      336
Pro Thr Trp Ser Met Ala Lys Leu Gln Leu Pro Met Leu Asn Glu Asp
            100                 105                 110 ctc acg tct gac acc cta caa atg tgg gag gca gtc tca gtg aaa acc      384
```

|  |  |  |  |  |  |  |  |  |  |  |  |  |  |  |  |
|---|---|---|---|---|---|---|---|---|---|---|---|---|---|---|---|
| Leu | Thr | Ser | Asp | Thr | Leu | Gln | Met | Trp | Glu | Ala | Val | Ser | Val | Lys | Thr |
|  |  | 115 |  |  |  | 120 |  |  |  |  | 125 |  |  |  |  |

```
gag gtg gtg ggc tct ggc tca ctg tta gat gtg cat ggg ttc aac aaa     432
Glu Val Val Gly Ser Gly Ser Leu Leu Asp Val His Gly Phe Asn Lys
130             135                 140 ccc aca gat aca gta aac aca aaa gga att tcc act cca gtg gaa ggc     480
Pro Thr Asp Thr Val Asn Thr Lys Gly Ile Ser Thr Pro Val Glu Gly
145                 150                 155                 160 agc caa tat cat gtg ttt gct gtg ggc ggg gaa ccg ctt gac ctc cag     528
Ser Gln Tyr His Val Phe Ala Val Gly Gly Glu Pro Leu Asp Leu Gln
                165                 170                 175 gga ctt gtg aca gat gcc aga aca aaa tac aag gaa gaa ggg gta gta     576
Gly Leu Val Thr Asp Ala Arg Thr Lys Tyr Lys Glu Glu Gly Val Val
            180                 185                 190 aca atc aaa aca atc aca aag aag gac atg gtc aac aaa gac caa gtc     624
Thr Ile Lys Thr Ile Thr Lys Lys Asp Met Val Asn Lys Asp Gln Val
        195                 200                 205 ctg aat cca att agc aag gcc aag ctg gat aag gac gga atg tat cca     672
Leu Asn Pro Ile Ser Lys Ala Lys Leu Asp Lys Asp Gly Met Tyr Pro
    210                 215                 220 gtt gaa atc tgg cat cca gat cca gca aaa aat gag aac aca agg tac     720
Val Glu Ile Trp His Pro Asp Pro Ala Lys Asn Glu Asn Thr Arg Tyr
225                 230                 235                 240 ttt ggc aat tac act gga ggc acg tgc acc cca ccc gtc ctg cag ttc     768
Phe Gly Asn Tyr Thr Gly Gly Thr Cys Thr Pro Pro Val Leu Gln Phe
                245                 250                 255 aca aac acc ctg aca act gtg ctc cta gat gaa aat gga gtt ggg ccc     816
Thr Asn Thr Leu Thr Thr Val Leu Leu Asp Glu Asn Gly Val Gly Pro
            260                 265                 270 ctc agc aaa gga gaa ggt cta tac ctc tcg agc gta gat ata atg ggc     864
Leu Ser Lys Gly Glu Gly Leu Tyr Leu Ser Ser Val Asp Ile Met Gly
        275                 280                 285 tgg aga gtt aca aga aac tat gat gtc cat cac tgg aga ggg ctt ccc     912
Trp Arg Val Thr Arg Asn Tyr Asp Val His His Trp Arg Gly Leu Pro
    290                 295                 300 aga tat ttc aaa atc acc ctg aga aaa aga tgg gtc aaa aat ccc tat     960
Arg Tyr Phe Lys Ile Thr Leu Arg Lys Arg Trp Val Lys Asn Pro Tyr
305                 310                 315                 320 ccc atg gcc tcc ctc ata agt tcc ctt ttc aac aac atg ctc ccc caa    1008
Pro Met Ala Ser Leu Ile Ser Ser Leu Phe Asn Asn Met Leu Pro Gln
                325                 330                 335 gtg cag ggc caa ccc atg gaa ggg gag aac acc cag gta gag gag gtt    1056
Val Gln Gly Gln Pro Met Glu Gly Glu Asn Thr Gln Val Glu Glu Val
            340                 345                 350 aga gtg tat gat ggg act gaa cct gta ccg ggg gac cct gat atg acg    1104
Arg Val Tyr Asp Gly Thr Glu Pro Val Pro Gly Asp Pro Asp Met Thr
        355                 360                 365 cgc tat gtt gac cgc ttt gga aaa aca aag act gta ttt cct ccc ggg    1152
Arg Tyr Val Asp Arg Phe Gly Lys Thr Lys Thr Val Phe Pro Pro Gly
    370                 375                 380
```

<210> SEQ ID NO 2
<211> LENGTH: 384
<212> TYPE: PRT
<213> ORGANISM: Artificial Sequence
<220> FEATURE:
<223> OTHER INFORMATION: Description of Artificial Sequence:polyomavirus
    VP1 protein with exchange of all Cys to Ser and
    exchange of Thr 249 to Cys (PyVP1-CallS

```
Met Ala Pro Lys Arg Lys Ser Gly Val Ser Lys Ser Glu Thr Lys Ser
 1               5                  10                  15

Thr Lys Ala Ser Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
 50                  55                  60

Glu Ser Leu Thr Glu Gly Gly Gln Tyr Tyr Gly Trp Ser Arg Gly Ile
 65                  70                  75                  80

Asn Leu Ala Thr Ser Asp Thr Glu Asp Ser Pro Gly Asn Asn Thr Leu
                85                  90                  95

Pro Thr Trp Ser Met Ala Lys Leu Gln Leu Pro Met Leu Asn Glu Asp
            100                 105                 110

Leu Thr Ser Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
130                 135                 140

Pro Thr Asp Thr Val Asn Thr Lys Gly Ile Ser Thr Pro Val Glu Gly
145                 150                 155                 160

Ser Gln Tyr His Val Phe Ala Val Gly Gly Glu Pro Leu Asp Leu Gln
                165                 170                 175

Gly Leu Val Thr Asp Ala Arg Thr Lys Tyr Lys Glu Glu Gly Val Val
            180                 185                 190

Thr Ile Lys Thr Ile Thr Lys Asp Met Val Asn Lys Asp Gln Val
        195                 200                 205

Leu Asn Pro Ile Ser Lys Ala Lys Leu Asp Lys Asp Gly Met Tyr Pro
210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr Cys Thr Pro Pro Val Leu Gln Phe
                245                 250                 255

Thr Asn Thr Leu Thr Thr Val Leu Leu Asp Glu Asn Gly Val Gly Pro
            260                 265                 270

Leu Ser Lys Gly Glu Gly Leu Tyr Leu Ser Ser Val Asp Ile Met Gly
        275                 280                 285

Trp Arg Val Thr Arg Asn Tyr Asp Val His His Trp Arg Gly Leu Pro
290                 295                 300

Arg Tyr Phe Lys Ile Thr Leu Arg Lys Arg Trp Val Lys Asn Pro Tyr
305                 310                 315                 320

Pro Met Ala Ser Leu Ile Ser Ser Leu Phe Asn Asn Met Leu Pro Gln
                325                 330                 335

Val Gln Gly Gln Pro Met Glu Gly Glu Asn Thr Gln Val Glu Glu Val
            340                 345                 350

Arg Val Tyr Asp Gly Thr Glu Pro Val Pro Gly Asp Pro Asp Met Thr
        355                 360                 365

Arg Tyr Val Asp Arg Phe Gly Lys Thr Lys Thr Val Phe Pro Pro Gly
370                 375                 380
```

<210> SEQ ID NO 3
<211> LENGTH: 1176
<212> TYPE: DNA
<213> ORGANISM: Artificial Sequence
<220> FEATURE:
<223> OTHER INFORMATION: Description of Artificial Sequence:fusion of modified polyomavirus VP1 gene (PyVP1-CallS-T249C)
to protamine-like RNA binding domain from
H

```
                                                           -continued
tgc acc cca ccc gtc ctg cag ttc aca aac acc ctg aca act gtg ctc        816
Cys Thr Pro Pro Val Leu Gln Phe Thr Asn Thr Leu Thr Thr Val Leu
        260                 265                 270 cta gat gaa aat gga gtt ggg ccc ctc agc aaa gga gaa ggt cta tac        864
Leu Asp Glu Asn Gly Val Gly Pro Leu Ser Lys Gly Glu Gly Leu Tyr
            275                 280                 285 ctc tcg agc gta gat ata atg ggc tgg aga gtt aca aga aac tat gat        912
Leu Ser Ser Val Asp Ile Met Gly Trp Arg Val Thr Arg Asn Tyr Asp
        290                 295                 300 gtc cat cac tgg aga ggg ctt ccc aga tat ttc aaa atc acc ctg aga        960
Val His His Trp Arg Gly Leu Pro Arg Tyr Phe Lys Ile Thr Leu Arg
305                 310                 315                 320 aaa aga tgg gtc aaa aat ccc tat ccc atg gcc tcc ctc ata agt tcc       1008
Lys Arg Trp Val Lys Asn Pro Tyr Pro Met Ala Ser Leu Ile Ser Ser
                325                 330                 335 ctt ttc aac aac atg ctc ccc caa gtg cag ggc caa ccc atg gaa ggg       1056
Leu Phe Asn Asn Met Leu Pro Gln Val Gln Gly Gln Pro Met Glu Gly
            340                 345                 350 gag aac acc cag gta gag gag gtt aga gtg tat gat ggg act gaa cct       1104
Glu Asn Thr Gln Val Glu Glu Val Arg Val Tyr Asp Gly Thr Glu Pro
        355                 360                 365 gta ccg ggg gac cct gat atg acg cgc tat gtt gac cgc ttt gga aaa       1152
Val Pro Gly Asp Pro Asp Met Thr Arg Tyr Val Asp Arg Phe Gly Lys
    370                 375                 380 aca aag act gta ttt cct ccc ggg                                        1176
Thr Lys Thr Val Phe Pro Pro Gly
385                 390
```

<210> SEQ ID NO 4
<211> LENGTH: 392
<212> TYPE: PRT
<213> ORGANISM: Artificial Sequence
<220> FEATURE:
<223> OTHER INFORMATION: Description of Artificial Sequence:fusion of
      modified polyomavirus VP1 protein (PyVP1-CalIS-T249C)
      to protamine-like RNA binding domain from
      Hepatitis B virus p21.5 at the 5' end (111-PyVP1)
<220> FEATURE:
<221> NAME/KEY: DOMAIN
<222> LOCATION: (2)..(26)
<223> OTHER INFORMATION: RNA binding motif from Hepatitis B virus p21.5
      protein

<400> SEQUENCE: 4

```
Met Ala Arg Arg Arg Asp Arg Gly Arg Ser Arg Arg Arg Asp Arg Gly
  1               5                  10                  15

Arg Ser Arg Arg Arg Asp Arg Gly Arg Ser Ala Ser Pro Arg Pro Ala
                 20                  25                  30

Pro Val Pro Lys Leu Leu Ile Lys Gly Gly Met Glu Val Leu Asp Leu
             35                  40                  45

Val Thr Gly Pro Asp Ser Val Thr Glu Ile Glu Ala Phe Leu Asn Pro
         50                  55                  60

Arg Met Gly Gln Pro Pro Thr Pro Glu Ser Leu Thr Glu Gly Gly Gln
 65                  70                  75                  80

Tyr Tyr Gly Trp Ser Arg Gly Ile Asn Leu Ala Thr Ser Asp Thr Glu
                 85                  90                  95

Asp Ser Pro Gly Asn Asn Thr Leu Pro Thr Trp Ser Met Ala Lys Leu
            100                 105                 110

Gln Leu Pro Met Leu Asn Glu Asp Leu Thr Ser Asp Thr Leu Gln Met
        115                 120                 125

Trp Glu Ala Val Ser Val Lys Thr Glu Val Val Gly Ser Gly Ser Leu
```

-continued

```
                    130                 135                 140
Leu Asp Val His Gly Phe Asn Lys Pro Thr Asp Thr Val Asn Thr Lys
145                 150                 155                 160

Gly Ile Ser Thr Pro Val Glu Gly Ser Gln Tyr His Val Phe Ala Val
                165                 170                 175

Gly Gly Glu Pro Leu Asp Leu Gln Gly Leu Val Thr Asp Ala Arg Thr
                180                 185                 190

Lys Tyr Lys Glu Glu Gly Val Thr Ile Lys Thr Ile Thr Lys Lys
            195                 200                 205

Asp Met Val Asn Lys Asp Gln Val Leu Asn Pro Ile Ser Lys Ala Lys
210                 215                 220

Leu Asp Lys Asp Gly Met Tyr Pro Val Glu Ile Trp His Pro Asp Pro
225                 230                 235                 240

Ala Lys Asn Glu Asn Thr Arg Tyr Phe Gly Asn Tyr Thr Gly Gly Thr
                245                 250                 255

Cys Thr Pro Pro Val Leu Gln Phe Thr Asn Thr Leu Thr Thr Val Leu
                260                 265                 270

Leu Asp Glu Asn Gly Val Gly Pro Leu Ser Lys Gly Glu Gly Leu Tyr
                275                 280                 285

Leu Ser Ser Val Asp Ile Met Gly Trp Arg Val Thr Arg Asn Tyr Asp
290                 295                 300

Val His His Trp Arg Gly Leu Pro Arg Tyr Phe Lys Ile Thr Leu Arg
305                 310                 315                 320

Lys Arg Trp Val Lys Asn Pro Tyr Pro Met Ala Ser Leu Ile Ser Ser
                325                 330                 335

Leu Phe Asn Asn Met Leu Pro Gln Val Gln Gly Gln Pro Met Glu Gly
                340                 345                 350

Glu Asn Thr Gln Val Glu Glu Val Arg Val Tyr Asp Gly Thr Glu Pro
            355                 360                 365

Val Pro Gly Asp Pro Asp Met Thr Arg Tyr Val Asp Arg Phe Gly Lys
                370                 375                 380

Thr Lys Thr Val Phe Pro Pro Gly
385                 390
```

<210> SEQ ID NO 5
<211> LENGTH: 1176
<212> TYPE: DNA
<213> ORGANISM: Artificial Sequence
<220> FEATURE:
<223> OTHER INFORMATION: Description of Artificial Sequence:fusion of
    modified polyomavirus VP1 gene (PyVP1-CallS-T249C)
    to protamine-like DNA binding domain from
    Hepatitis B virus P21.5 at the 5' end (234

-continued

| | |
|---|---|
| ccc gtt ccc aaa ctg ctt att aaa ggg ggt atg gag gtg ctg gac ctt<br>Pro Val Pro Lys Leu Leu Ile Lys Gly Gly Met Glu Val Leu Asp Leu<br>      35                      40                        45 | 144 |
| gtg aca ggg cca gac agt gtg aca gaa ata gaa gct ttt ctg aac ccc<br>Val Thr Gly Pro Asp Ser Val Thr Glu Ile Glu Ala Phe Leu Asn Pro<br>50                      55                      60 | 192 |
| aga atg ggg cag cca ccc acc cct gaa agc cta aca gag gga ggg caa<br>Arg Met Gly Gln Pro Pro Thr Pro Glu Ser Leu Thr Glu Gly Gly Gln<br>65                      70                      75                      80 | 240 |
| tac tat ggt tgg agc aga ggg att aat ttg gct aca tca gat aca gag<br>Tyr Tyr Gly Trp Ser Arg Gly Ile Asn Leu Ala Thr Ser Asp Thr Glu<br>                      85                      90                      95 | 288 |
| gat tcc cca gga aat aat aca ctt ccc aca tgg agt atg gca aag ctc<br>Asp Ser Pro Gly Asn Asn Thr Leu Pro Thr Trp Ser Met Ala Lys Leu<br>              100                      105                      110 | 336 |
| cag ctt ccc atg ctc aat gag gac ctc acg tct gac acc cta caa atg<br>Gln Leu Pro Met Leu Asn Glu Asp Leu Thr Ser Asp Thr Leu Gln Met<br>              115                      120                      125 | 384 |
| tgg gag gca gtc tca gtg aaa acc gag gtg gtg ggc tct ggc tca ctg<br>Trp Glu Ala Val Ser Val Lys Thr Glu Val Val Gly Ser Gly Ser Leu<br>130                      135                      140 | 432 |
| tta gat gtg cat ggg ttc aac aaa ccc aca gat aca gta aac aca aaa<br>Leu Asp Val His Gly Phe Asn Lys Pro Thr Asp Thr Val Asn Thr Lys<br>145                      150                      155                      160 | 480 |
| gga att tcc act cca gtg gaa ggc agc caa tat cat gtg ttt gct gtg<br>Gly Ile Ser Thr Pro Val Glu Gly Ser Gln Tyr His Val Phe Ala Val<br>              165                      170                      175 | 528 |
| ggc ggg gaa ccg ctt gac ctc cag gga ctt gtg aca gat gcc aga aca<br>Gly Gly Glu Pro Leu Asp Leu Gln Gly Leu Val Thr Asp Ala Arg Thr<br>              180                      185                      190 | 576 |
| aaa tac aag gaa gaa ggg gta gta aca atc aaa aca atc aca aag aag<br>Lys Tyr Lys Glu Glu Gly Val Val Thr Ile Lys Thr Ile Thr Lys Lys<br>              195                      200                      205 | 624 |
| gac atg gtc aac aaa gac caa gtc ctg aat cca att agc aag gcc aag<br>Asp Met Val Asn Lys Asp Gln Val Leu Asn Pro Ile Ser Lys Ala Lys<br>210                      215                      220 | 672 |
| ctg gat aag gac gga atg tat cca gtt gaa atc tgg cat cca gat cca<br>Leu Asp Lys Asp Gly Met Tyr Pro Val Glu Ile Trp His Pro Asp Pro<br>225                      230                      235                      240 | 720 |
| gca aaa aat gag aac aca agg tac ttt ggc aat tac act gga ggc acg<br>Ala Lys Asn Glu Asn Thr Arg Tyr Phe Gly Asn Tyr Thr Gly Gly Thr<br>              245                      250                      255 | 768 |
| tgc acc cca ccc gtc ctg cag ttc aca aac acc ctg aca act gtg ctc<br>Cys Thr Pro Pro Val Leu Gln Phe Thr Asn Thr Leu Thr Thr Val Leu<br>              260                      265                      270 | 816 |
| cta gat gaa aat gga gtt ggg ccc ctc agc aaa gga gaa ggt cta tac<br>Leu Asp Glu Asn Gly Val Gly Pro Leu Ser Lys Gly Glu Gly Leu Tyr<br>              275                      280                      285 | 864 |
| ctc tcg agc gta gat ata atg ggc tgg aga gtt aca aga aac tat gat<br>Leu Ser Ser Val Asp Ile Met Gly Trp Arg Val Thr Arg Asn Tyr Asp<br>              290                      295                      300 | 912 |
| gtc cat cac tgg aga ggg ctt ccc aga tat ttc aaa atc acc ctg aga<br>Val His His Trp Arg Gly Leu Pro Arg Tyr Phe Lys Ile Thr Leu Arg<br>305                      310                      315                      320 | 960 |
| aaa aga tgg gtc aaa aat ccc tat ccc atg gcc tcc ctc ata agt tcc<br>Lys Arg Trp Val Lys Asn Pro Tyr Pro Met Ala Ser Leu Ile Ser Ser<br>              325                      330                      335 | 1008 |
| ctt ttc aac aac atg ctc ccc caa gtg cag ggc caa ccc atg gaa ggg<br>Leu Phe Asn Asn Met Leu Pro Gln Val Gln Gly Gln Pro Met Glu Gly | 1056 |

-continued

```
            340                 345                 350
gag aac acc cag gta gag gag gtt aga gtg tat gat ggg act gaa cct      1104
Glu Asn Thr Gln Val Glu Glu Val Arg Val Tyr Asp Gly Thr Glu Pro
            355                 360                 365 gta ccg ggg gac cct gat atg acg cgc tat gtt gac cgc ttt gga aaa      1152
Val Pro Gly Asp Pro Asp Met Thr Arg Tyr Val Asp Arg Phe Gly Lys
    370                 375                 380 aca aag act gta ttt cct ccc ggg                                      1176
Thr Lys Thr Val Phe Pro Pro Gly
385                 390
```

<210> SEQ ID NO 6
<211> LENGTH: 392
<212> TYPE: PRT
<213> ORGANISM: Artificial Sequence
<220> FEATURE:
<223> OTHER INFORMATION: Description of Artificial Sequence:fusion of
      modified polyomavirus VP1 protein (PyVP1-CallS-T249C)
      to prot -continued

```
Cys Thr Pro Pro Val Leu Gln Phe Thr Asn Thr Leu Thr Thr Val Leu
            260                 265                 270

Leu Asp Glu Asn Gly Val Gly Pro Leu Ser Lys Gly Glu Gly Leu Tyr
        275                 280                 285

Leu Ser Ser Val Asp Ile Met Gly Trp Arg Val Thr Arg Asn Tyr Asp
        290                 295                 300

Val His His Trp Arg Gly Leu Pro Arg Tyr Phe Lys Ile Thr Leu Arg
305                 310                 315                 320

Lys Arg Trp Val Lys Asn Pro Tyr Pro Met Ala Ser Leu Ile Ser Ser
                325                 330                 335

Leu Phe Asn Asn Met Leu Pro Gln Val Gln Gly Gln Pro Met Glu Gly
            340                 345                 350

Glu Asn Thr Gln Val Glu Val Arg Val Tyr Asp Gly Thr Glu Pro
            355                 360                 365

Val Pro Gly Asp Pro Asp Met Thr Arg Tyr Val Asp Arg Phe Gly Lys
        370                 375                 380

Thr Lys Thr Val Phe Pro Pro Gly
385                 390

<210> SEQ ID NO 7
<211> LENGTH: 765
<212> TYPE: DNA
<213> ORGANISM: Artificial Sequence
<220> FEATURE:
<223> OTHER INFORMATION: Description of Artificial Sequence:enhanced
      green fluorescent protein (GFP) with fused C-terminal
      proline-rich sequence (GFP-PPLP)
<220> FEATURE:
<221> NAME/KEY: CDS
<222> LOCATION: (1)..(765)
<223> OTHER INFORMATION: GFP-PPLP
<220> FEATURE:
<221> NAME/KEY: misc_feature
<222> LOCATION: (736)..(765)
<223> OTHER INFORMATION: proline-rich sequence insert

<400> SEQUENCE: 7 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125
```

```
atc gac ttc aag gag gac ggc aac atc ctg ggg cac aag ctg gag tac        432
Ile Asp Phe Lys Glu Asp Gly Asn Ile Leu Gly His Lys Leu Glu Tyr
            130                 135                 140 aac tac aac agc cac aac gtc tat atc atg gcc gac aag cag aag aac        480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc        528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc        576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg        624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc        672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac tta agc        720
Val Thr Ala Ala Gly Ile Thr Leu Gly Met Asp Glu Leu Tyr Leu Ser
225                 230                 235                 240 cga cgt gcc tca ggt ccg ccg cct cca ccg cca ccg cct tta ccc            765
Arg Arg Ala Ser Gly Pro Pro Pro Pro Pro Pro Pro Leu Pro
                245                 250                 255

<210> SEQ ID NO 8
<211> LENGTH: 255
<212> TYPE: PRT
<213> ORGANISM: Artificial Sequence
<220> FEATURE:
<223> OTHER INFORMATION: Description of Artificial Sequence:enhanced
      green fluorescent protein (GFP) with fused C-terminal
      proline-rich sequence (GFP-PPLP)
<220> FEATURE:
<221> NAME/KEY: PEPTIDE
<222> LOCATION: (246)..(255)
<223> OTHER INFORMATION: C-terminal proline-rich sequence

<400> SEQUENCE: 8

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

-continued

```
Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Leu Ser
225                 230                 235                 240

Arg Arg Ala Ser Gly Pro Pro Pro Pro Pro Pro Pro Leu Pro
                245                 250                 255
```

<210> SEQ ID NO 9
<211> LENGTH: 1251
<212> TYPE: DNA
<213> ORGANISM: Artificial Sequence
<220> FEATURE:
<223> OTHER INFORMATION: Description of Artificial Sequence:polyomavirus
      VP1 gene with 4 of 6 Cys replaced by Ser and
      exchange of VP1 Thr 249 to Cys fused with
      N-terminal WW domain (PyVP1-WW1)
<220> FEATURE:
<221> NAME/KEY: CDS
<222> LOCATION: (1)..(1251)
<223> OTHER INFORMATION: PyVP1-WW1
<220> FEATURE:
<221> NAME/KEY: misc_feature
<222> LOCATION: (10)..(93)
<223> OTHER INFORMATION: WW domain insert

<400> SEQUENCE: 9

```
atg agc ggc tgg aca gaa cat aaa tca cct gat gga agg act tat tat        48
Met Ser Gly Trp Thr Glu His Lys Ser Pro Asp Gly Arg Thr Tyr Tyr
1               5                   10                  15 tac aat act gaa aca aaa cag tct acc tgg gaa aag cca gat gat gga        96
Tyr Asn Thr Glu Thr Lys Gln Ser Thr Trp Glu Lys Pro Asp Asp Gly
                20                  25                  30 cat atg gcc ccc aaa aga aaa agc ggc gtc tct aaa tct gag aca aaa       144
His Met Ala Pro Lys Arg Lys Ser Gly Val Ser Lys Ser Glu Thr Lys
            35                  40                  45 agc aca aag gcc tgt cca aga ccc gca ccc gtt ccc aaa ctg ctt att       192
Ser Thr Lys Ala Cys Pro Arg Pro Ala Pro Val Pro Lys Leu Leu Ile
        50                  55                  60 aaa ggg ggt atg gag gtg ctg gac ctt gtg aca ggg cca gac agt gtg       240
Lys Gly Gly Met Glu Val Leu Asp Leu Val Thr Gly Pro Asp Ser Val
65                  70                  75                  80 aca gaa ata gaa gct ttt ctg aac ccc aga atg ggg cag cca ccc acc       288
Thr Glu Ile Glu Ala Phe Leu Asn Pro Arg Met Gly Gln Pro Pro Thr
                85                  90                  95 cct gaa agc cta aca gag gga ggg caa tac tat ggt tgg agc aga ggg       336
Pro Glu Ser Leu Thr Glu Gly Gly Gln Tyr Tyr Gly Trp Ser Arg Gly
            100                 105                 110 att aat ttg gct aca tca gat aca gag gat tcc cca gga aat aat aca       384
Ile Asn Leu Ala Thr Ser Asp Thr Glu Asp Ser Pro Gly Asn Asn Thr
        115                 120                 125 ctt ccc aca tgg agt atg gca aag ctc cag ctt ccc atg ctc aat gag       432
Leu Pro Thr Trp Ser Met Ala Lys Leu Gln Leu Pro Met Leu Asn Glu
    130                 135                 140 gac ctc acc tgt gac acc cta caa atg tgg gag gca gtc tca gtg aaa       480
Asp Leu Thr Cys Asp Thr Leu Gln Met Trp Glu Ala Val Ser Val Lys
145                 150                 155                 160
```

| | | |
|---|---|---|
| acc gag gtg gtg ggc tct ggc tca ctg tta gat gtg cat ggg ttc aac<br>Thr Glu Val Val Gly Ser Gly Ser Leu Leu Asp Val His Gly Phe Asn<br>165 170 175 | | 528 |
| aaa ccc aca gat aca gta aac aca aaa gga att tcc act cca gtg gaa<br>Lys Pro Thr Asp Thr Val Asn Thr Lys Gly Ile Ser Thr Pro Val Glu<br>180 185 190 | | 576 |
| ggc agc caa tat cat gtg ttt gct gtg ggc ggg gaa ccg ctt gac ctc<br>Gly Ser Gln Tyr His Val Phe Ala Val Gly Gly Glu Pro Leu Asp Leu<br>195 200 205 | | 624 |
| cag gga ctt gtg aca gat gcc aga aca aaa tac aag gaa gaa ggg gta<br>Gln Gly Leu Val Thr Asp Ala Arg Thr Lys Tyr Lys Glu Glu Gly Val<br>210 215 220 | | 672 |
| gta aca atc aaa aca atc aca aag aag gac atg gtc aac aaa gac caa<br>Val Thr Ile Lys Thr Ile Thr Lys Lys Asp Met Val Asn Lys Asp Gln<br>225 230 235 240 | | 720 |
| gtc ctg aat cca att agc aag gcc aag ctg gat aag gac gga atg tat<br>Val Leu Asn Pro Ile Ser Lys Ala Lys Leu Asp Lys Asp Gly Met Tyr<br>245 250 255 | | 768 |
| cca gtt gaa atc tgg cat cca gat cca gca aaa aat gag aac aca agg<br>Pro Val Glu Ile Trp His Pro Asp Pro Ala Lys Asn Glu Asn Thr Arg<br>260 265 270 | | 816 |
| tac ttt ggc aat tac act gga ggc acg tgc acc cca ccc gtc ctg cag<br>Tyr Phe Gly Asn Tyr Thr Gly Gly Thr Cys Thr Pro Pro Val Leu Gln<br>275 280 285 | | 864 |
| ttc aca aac acc ctg aca act gtg ctc cta gat gaa aat gga gtt ggg<br>Phe Thr Asn Thr Leu Thr Thr Val Leu Leu Asp Glu Asn Gly Val Gly<br>290 295 300 | | 912 |
| ccc ctc agc aaa gga gag ggc cta tac ctc tcg agc gta gat ata atg<br>Pro Leu Ser Lys Gly Glu Gly Leu Tyr Leu Ser Ser Val Asp Ile Met<br>305 310 315 320 | | 960 |
| ggc tgg aga gtt aca aga aac tat gat gtc cat cac tgg aga ggg ctt<br>Gly Trp Arg Val Thr Arg Asn Tyr Asp Val His His Trp Arg Gly Leu<br>325 330 335 | | 1008 |
| ccc aga tat ttc aaa atc acc ctg aga aaa aga tgg gtc aaa aat ccc<br>Pro Arg Tyr Phe Lys Ile Thr Leu Arg Lys Arg Trp Val Lys Asn Pro<br>340 345 350 | | 1056 |
| tat ccc atg gcc tcc ctc ata agt tcc ctt ttc aac aac atg ctc ccc<br>Tyr Pro Met Ala Ser Leu Ile Ser Ser Leu Phe Asn Asn Met Leu Pro<br>355 360 365 | | 1104 |
| caa gtg cag ggc caa ccc atg gaa ggg gag aac acc cag gta gag gag<br>Gln Val Gln Gly Gln Pro Met Glu Gly Glu Asn Thr Gln Val Glu Glu<br>370 375 380 | | 1152 |
| gtt aga gtg tat gat ggg act gaa cct gta ccg ggg gac cct gat atg<br>Val Arg Val Tyr Asp Gly Thr Glu Pro Val Pro Gly Asp Pro Asp Met<br>385 390 395 400 | | 1200 |
| acg cgc tat gtt gac cgc ttt gga aaa aca aag act gta ttt cct ccc<br>Thr Arg Tyr Val Asp Arg Phe Gly Lys Thr Lys Thr Val Phe Pro Pro<br>405 410 415 | | 1248 |
| ggg<br>Gly | | 1251 |

<210> SEQ ID NO 10
<211> LENGTH: 417
<212> TYPE: PRT
<213> ORGANISM: Artificial Sequence
<220> FEATURE:
<223> OTHER INFORMATION: Description of Artificial Sequence:polyomavirus
      VP1 protein with 4 of 6 Cys replaced by Ser and
      exchange of VP1 Thr 249 to Cys fused with
      N-terminal WW domain (PyVP1-WW1)
<220> FEATURE:
<221> NAME/KEY: DOMAIN
<222> LOCATION: (5)..(31)
<223> OTHER INFORMATION: WW domain insert

<400> SEQUENCE: 10

Met Ser Gly Trp Thr Glu His Lys Ser Pro Asp Gly Arg Thr Tyr Tyr
1               5                   10                  15

Tyr Asn Thr Glu Thr Lys Gln Ser Thr Trp Glu Lys Pro Asp Asp Gly
                20                  25                  30

His Met Ala Pro Lys Arg Lys Ser Gly Val Ser Lys Ser Glu Thr Lys
            35                  40                  45

Ser Thr Lys Ala Cys Pro Arg Pro Ala Pro Val Pro Lys Leu Leu Ile
    50                  55                  60

Lys Gly Gly Met Glu Val Leu Asp Leu Val Thr Gly Pro Asp Ser Val
65              70                  75                  80

Thr Glu Ile Glu Ala Phe Leu Asn Pro Arg Met Gly Gln Pro Pro Thr
                85                  90                  95

Pro Glu Ser Leu Thr Glu Gly Gly Gln Tyr Tyr Gly Trp Ser Arg Gly
            100                 105                 110

Ile Asn Leu Ala Thr Ser Asp Thr Glu Asp Ser Pro Gly Asn Asn Thr
        115                 120                 125

Leu Pro Thr Trp Ser Met Ala Lys Leu Gln Leu Pro Met Leu Asn Glu
130                 135                 140

Asp Leu Thr Cys Asp Thr Leu Gln Met Trp Glu Ala Val Ser Val Lys
145                 150                 155                 160

Thr Glu Val Val Gly Ser Gly Ser Leu Leu Asp Val His Gly Phe Asn
                165                 170                 175

Lys Pro Thr Asp Thr Val Asn Thr Lys Gly Ile Ser Thr Pro Val Glu
            180                 185                 190

Gly Ser Gln Tyr His Val Phe Ala Val Gly Gly Glu Pro Leu Asp Leu
        195                 200                 205

Gln Gly Leu Val Thr Asp Ala Arg Thr Lys Tyr Lys Glu Glu Gly Val
    210                 215                 220

Val Thr Ile Lys Thr Ile Thr Lys Lys Asp Met Val Asn Lys Asp Gln
225                 230                 235                 240

Val Leu Asn Pro Ile Ser Lys Ala Lys Leu Asp Lys Asp Gly Met Tyr
                245                 250                 255

Pro Val Glu Ile Trp His Pro Asp Pro Ala Lys Asn Glu Asn Thr Arg
            260                 265                 270

Tyr Phe Gly Asn Tyr Thr Gly Gly Thr Cys Thr Pro Pro Val Leu Gln
        275                 280                 285

Phe Thr Asn Thr Leu Thr Thr Val Leu Leu Asp Glu Asn Gly Val Gly
    290                 295                 300

Pro Leu Ser Lys Gly Glu Gly Leu Tyr Leu Ser Ser Val Asp Ile Met
305                 310                 315                 320

Gly Trp Arg Val Thr Arg Asn Tyr Asp Val His His Trp Arg Gly Leu
                325                 330                 335

Pro Arg Tyr Phe Lys Ile Thr Leu Arg Lys Arg Trp Val Lys Asn Pro
            340                 345                 350

Tyr Pro Met Ala Ser Leu Ile Ser Ser Leu Phe Asn Asn Met Leu Pro
        355                 360                 365

Gln Val Gln Gly Gln Pro Met Glu Gly Glu Asn Thr Gln Val Glu Glu
    370                 375                 380

Val Arg Val Tyr Asp Gly Thr Glu Pro Val Pro Gly Asp Pro Asp Met
385                 390                 395                 400

```
Thr Arg Tyr Val Asp Arg Phe Gly Lys Thr Lys Thr Val Phe Pro Pro
            405                 410                 415
Gly

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:
      oligonucleotide PCR primer

<400> SEQUENCE: 11
tatacatatg gcccccaaaa gaaaaagc                                    28

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:
      oligonucleotide PCR primer

<400> SEQUENCE: 12
atatcccggg aggaaataca gtctttgttt ttcc                             34

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:PCR
      oligonucleotides

<400> SEQUENCE: 13
tatacatatg gcccccaaaa gaaaaagc                                    28

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:PCR
      oligonucleotides

<400> SEQUENCE: 14
atatgaattc cagtcattga agctgccaca agg                              33

<210> SEQ ID NO 15
<211> LENGTH: 78
<212> TYPE: DNA
<213> ORGANISM: Artificial Sequence
<220> FEATURE:
<223> OTHER INFORMATION: Description of Artificial Sequence:synthetic
      double-stranded 78-bp oligonucleotide

<400> SEQUENCE: 15
atggccagcc cgcgtcgtcg taccccaagc ccacgtcgtc gtcgtagcca gagcccgcgg   60
tcgtccggtc gtagccag                                                78

<210> SEQ ID NO 16
<211> LENGTH: 18
<212> TYPE: PRT
<213> ORGANISM: Artificial Sequence
<220> FEATURE:
```

```
<223> OTHER INFORMATION: Description of Artificial Sequence:first amino
      acids of PyVP1 protein

<400> SEQUENCE: 16

Met Ala Pro Lys Arg Lys Ser Gly Val Ser Lys Ser Glu Thr Lys Ser
 1               5                  10                  15

Thr Lys

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence:234 sequence
      encoded by 78-bp oligonucleotide

<400> SEQUENCE: 17

Met Ala Ser Pro Arg Arg Thr Pro Ser Pro Arg Arg Arg Ser
 1               5                  10                  15

Gln Ser Pro Arg Arg Arg Arg Ser Gln
            20                  25

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence:111 sequence

<400> SEQUENCE: 18

Met Ala Arg Arg Arg Asp Arg Gly Arg Ser Arg Arg Arg Asp Arg Gly
 1               5                  10                  15

Arg Ser Arg Arg Arg Asp Arg Gly Arg Ser
            20                  25

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence:synthetic
      double-stranded oligonucleotide

<400> SEQUENCE: 19
atggcgcgtc gtcgtgatcg tggccgtagc cgtcgtcgtg atcgtggtcg tagccgtcgt      60
cgtgatcgtg gtcgtagc                                                    78

<210> SEQ ID NO 20
<211> LENGTH: 31
<212> TYPE: PRT
<213> ORGANISM: Artificial Sequence
<220> FEATURE:
<223> OTHER INFORMATION: Description of Artificial Sequence:WW domain
      from mouse FBP11 gene

<400> SEQUENCE: 20

Gly Ser Gly Trp Thr Glu His Lys Ser Pro Asp Gly Arg Thr Tyr Tyr
 1               5                  10                  15

Tyr Asn Thr Glu Thr Lys Gln Ser Thr Trp Glu Lys Pro Asp Asp
            20                  25                  30

<210> SEQ ID NO 21
<211> LENGTH: 4
<212> TYPE: PRT
```

```
<213> ORGANISM: Artificial Sequence
<220> FEATURE:
<223> OTHER INFORMATION: Description of Artificial Sequence:peptide
      sequence with high affinity to FBP11 WW domain

<400> SEQUENCE: 21

Pro Pro Leu Pro
  1

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence:PCR
      oligonucleotide

<400> SEQUENCE: 22
aatatatcat atgtccatca tccggctttt cccaggtaga ct                          42

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence:PCR
      oligonucleotide

<400> SEQUENCE: 23
tattaatcat atgagcggct ggacagaaca taaatcacct gatgg                       45

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence:PCR
      oligonucleotide

<400> SEQUENCE: 24
ttatttacat atggtgagca agggcgagga g                                      31

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence:PCR
      oligonucleotide

<400> SEQUENCE: 25
atatcttaag tacagctcgt ccatgccg                                          28

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence:proline-rich
      sequence

<400> SEQUENCE: 26

Pro Pro Pro Pro Pro Pro Pro Pro Leu Pro
  1               5                  10
```